(12) United States Patent
Weaver et al.

(10) Patent No.: US 10,767,209 B2
(45) Date of Patent: Sep. 8, 2020

(54) DEVICE AND METHOD FOR DETECTING PLANT PATHOGENS

(71) Applicant: FungiAlert Limited, Harpenden, Hertfordshire (GB)

(72) Inventors: Kerry O'Donnelly Weaver, Harpenden (GB); Angela De Manzanos Guinot, Harpenden (GB)

(73) Assignee: FUNGIALERT LIMITED, Harpenden (GB)

( * ) Notice: Subject to any disclaimer, the term of this patent is extended or adjusted under 35 U.S.C. 154(b) by 0 days.

(21) Appl. No.: 15/536,825

(22) PCT Filed: Dec. 16, 2015

(86) PCT No.: PCT/GB2015/054036
§ 371 (c)(1),
(2) Date: Jun. 16, 2017

(87) PCT Pub. No.: WO2016/097726
PCT Pub. Date: Jun. 23, 2016

(65) Prior Publication Data
US 2017/0349931 A1    Dec. 7, 2017

(30) Foreign Application Priority Data
Dec. 16, 2014 (GB) .................................. 1422390.3

(51) Int. Cl.
*C12Q 1/04* (2006.01)
(52) U.S. Cl.
CPC .......... *C12Q 1/04* (2013.01); *G01N 2333/37* (2013.01)
(58) Field of Classification Search
CPC ...................................................... C12Q 1/04
See application file for complete search history.

(56) References Cited

U.S. PATENT DOCUMENTS

| 5,817,472 A | 10/1998 | Hardham et al. |
| 2009/0325219 A1 | 12/2009 | Williamson et al. |
| 2011/0275112 A1 | 11/2011 | Sarver, Jr. et al. |

FOREIGN PATENT DOCUMENTS

| CN | 103305404 B | 11/2014 |
| WO | 2008/017861 A1 | 2/2008 |
| WO | 2011/139263 A1 | 11/2011 |
| WO | 94/08042 A1 | 11/2014 |

OTHER PUBLICATIONS

Cahill et al. Phytopathology, 1994, 84:193-200.*
Barton et al. Applied and Environmental Microbiology, 1995, 61(9):3329-3335.*
Rioux et al. Can. J. Plant Pathol., 2014, 36(2):235-245.*
International Search Report and Written Opinion from the European Patent Office for Application No. PCT/GB2015/054036, dated Nov. 2, 2016.

* cited by examiner

*Primary Examiner* — Bin Shen
(74) *Attorney, Agent, or Firm* — The Dobrusin Law Firm, P.C.; Bryan S. Lemanski

(57) ABSTRACT

The present invention relates to a device for detecting a plant pathogen spore in soil or water. The present invention also relates to a method for detection of a plant pathogen spore. The device for detecting a plant pathogen spore in soil or water comprises a support member containing a plant pathogen chemoattractant; a filter having a plurality of pores; a culture medium containing a plant pathogen chemoattractant; and a detection means; wherein the support member is adjacent to the filter and the filter is adjacent to the culture medium.

15 Claims, 5 Drawing Sheets

A)

B)

US 10,767,209 B2

DEVICE AND METHOD FOR DETECTING PLANT PATHOGENS

FIELD OF THE INVENTION

Figure 1:
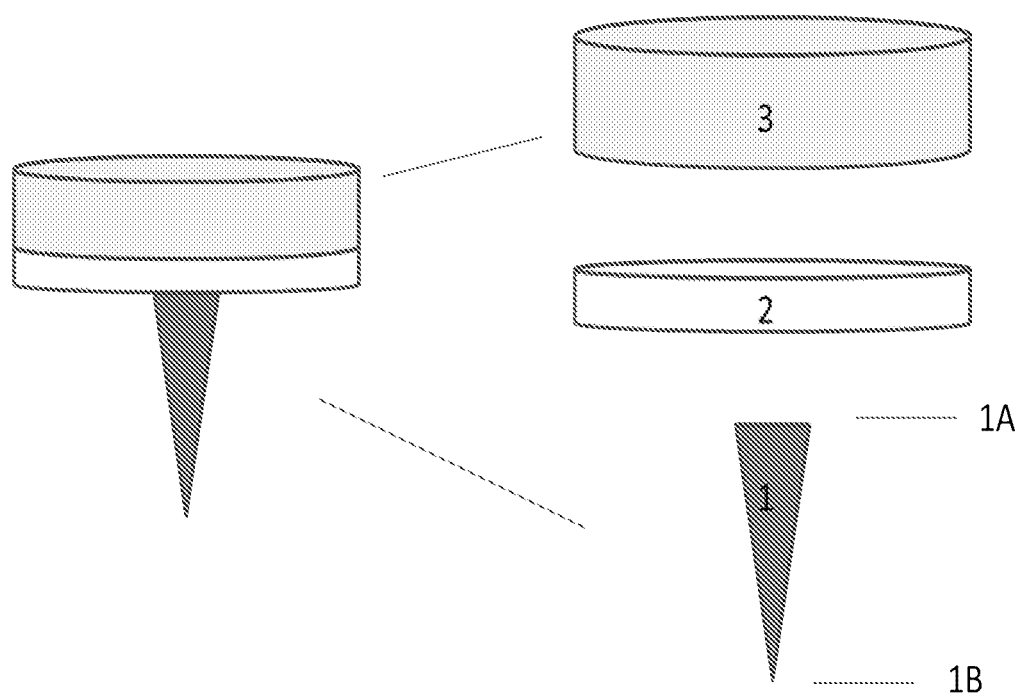

The present invention relates to a device for detecting a plant pathogen spore in soil or water. The present invention also relates to a method for detection of a plant pathogen spore.

BACKGROUND TO THE INVENTION

Loss of plant yield due to plant disease is a global concern, not only in agriculture and horticulture but also in ornamental plants. Many valuable crop and ornamental plants are very susceptible to disease and would have difficulty surviving in nature without human intervention.

Cultivated plants are often more susceptible to disease than their wild relatives because large numbers of the same species or variety (which have a uniform genetic background), are grown closely together, sometimes over many thousands of square kilometres. A pathogen may spread rapidly under these conditions. For example, *Phytophthora*, a soil borne plant pathogen attacks the roots and stems of a range of plants, vegetable and fruits, is of particular concern to growers as it can contaminate water supplies and can also stay undetected in plant debris and soil for many years. It is estimated that *Phytophthora*, known as the "Plant Destroyer of the 21st Century", alone causes a $2-7 billion loss per crop per year worldwide (Roy et al., 2012 *Review of Plant Pathology*, Vol 6).

Numerous methods exist to detect plant pathogens. Farmers typically use consultant agronomists who take a sample of soil or plant material, for example the leaf or root, and analyse the sample for plant pathogens. Analysis is conducted externally using laboratory tests. Such laboratory tests can include molecular techniques such as ELISA, PCR (PCR and real-time PCR), immunofluorescence (IF), flow cytometry, fluorescence in situ hybridization (FISH), and DNA microarrays. There are several problems with external laboratory testing of samples. Firstly, soil sampling selects only a small sample and may not necessarily reflect the true condition of the soil.

In some cases, the level of pathogen to be detected in the soil will be too low, therefore sampling an isolated area of soil the level of plant pathogen will be too low to be detected. External laboratory analysis requires transportation of samples away from the testing site to a laboratory and therefore there is a delay in providing the result of the diagnostic analysis. Any delay in detecting a plant pathogen can lead to further spread of the plant pathogen and a greater number of plants being affected.

Samples can also be tested for plant pathogens on site using lateral flow devices. Such devices require the farmer to take a sample from a plant, for example a leaf. The device extracts proteins in the plant sample and the presence of a plant pathogen can be detected. Each plant sample is representative only for the plant being tested. Each sample is therefore not representative of the entire plant growth area. Further, a plant sample that tests positive for a plant pathogen indicates the plant has already been affected by the pathogen. This may be too late to prevent spread of the plant pathogen to surrounding plants.

In some instances, the farmer may not detect plant pathogens at all and simply utilises preventative spraying routines against common plant pathogens. It is not known if the plants will be targeted by a plant pathogen if left untreated and therefore such spraying routines may be unnecessary in some cases and an unnecessary cost.

Early detection of plant health and disease could facilitate the control of disease through proper management strategies, such as vector control through pesticide applications, fungicide applications and disease-specific chemical applications. There is a need to provide an accurate and simple method or device for detecting a plant pathogen that can be utilised at the site of plant growth.

SUMMARY OF THE INVENTION

The present inventors have developed a device that detects a plant pathogen spore in soil or water. The device of the present invention is robust, cost-effective and easier to use than current products on the market. The device does not require manual preparation of the soil sample and can be easily installed and utilized at the site of testing for the plant pathogen. The device of the present invention does not require external laboratory analysis and instead can be used at the site to be sampled. This may result in early detection of the plant pathogen.

Accordingly, in a first aspect the present invention provides a device for detecting a plant pathogen spore in soil or water comprising: a support member (1) containing at least one plant pathogen chemoattractant; a filter (2) having a plurality of pores; a culture medium (3) containing at least one plant pathogen chemoattractant; and a detection means; wherein the support member (1) is adjacent to the filter (2) and the filter (2) is adjacent to the culture medium (3). In a preferred embodiment, the detection means is a pH indicator.

The device of the present invention allows for testing over a wider area, as the pathogen will be attracted to the at least one plant pathogen chemoattractant, causing it to travel to the device and concentrate there, allowing for a higher sensitivity detection device than current methods.

A further advantage of the device of the present invention is that it not only acts as a detection device but also as a deterrent to plant pathogens. The plant pathogen being detected will be attracted to the at least one plant pathogen chemoattractant within the detection device of the present invention and will therefore travel to the detection device rather than the surrounding soil.

DETAILED DESCRIPTION OF THE INVENTION

Embodiments will now be described, by way of example, with reference to FIGS. 1 to 5:

FIG. 1 illustrates a side view of a detection device in accordance with an embodiment of the invention in which 1 is a support member that contains a plant pathogen chemoattractant, the support member having two ends, 1A and 1B, 2 is a filter comprising pores and 3 is a culture medium comprising a plant pathogen chemoattractant and a detection means. The detection means can optionally be a pH indicator.

Figure 2:
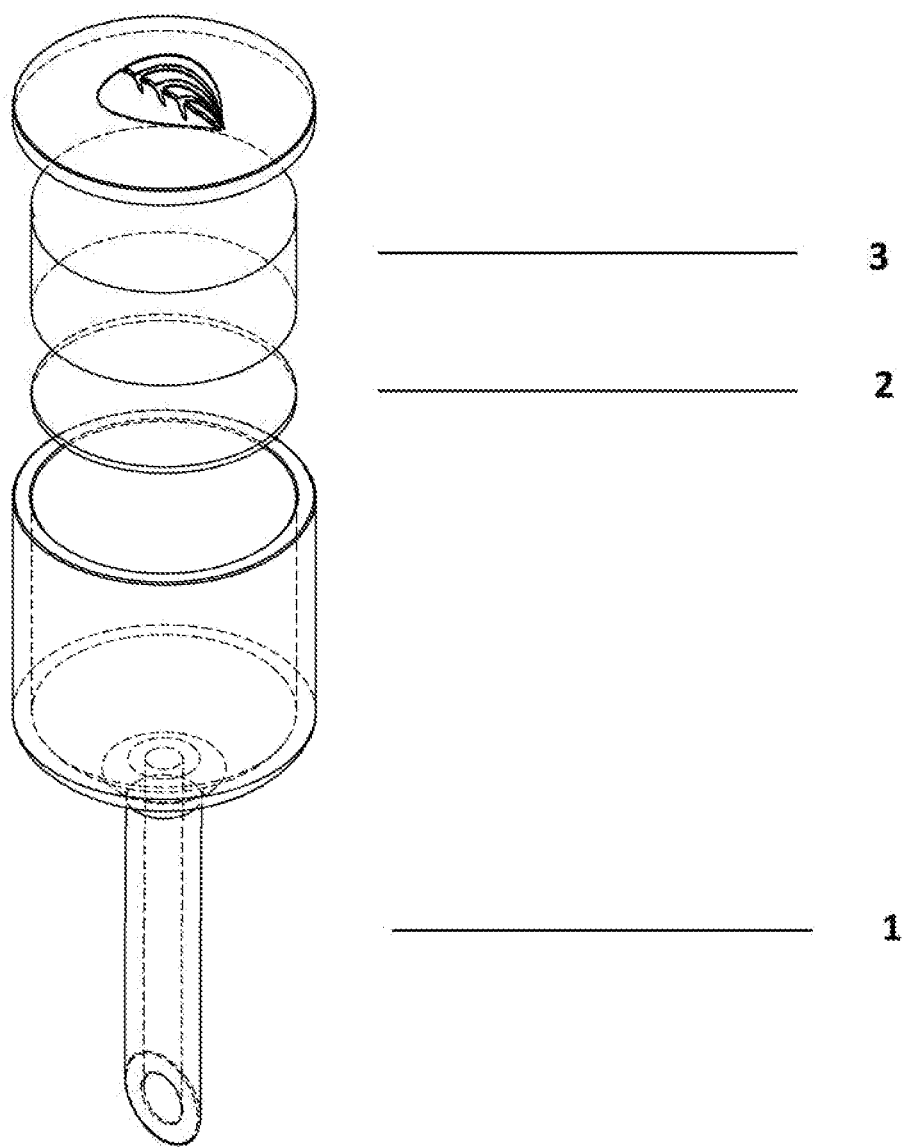

FIG. 2 illustrates a three-dimensional representation of a detection device in accordance with an embodiment of the invention in which 1 is a support member that contains a plant pathogen chemoattractant, 2 is a filter comprising pores and 3 is a culture medium comprising a plant pathogen chemoattractant and a detection means. The detection means can optionally be a pH indicator.

Figure 3:
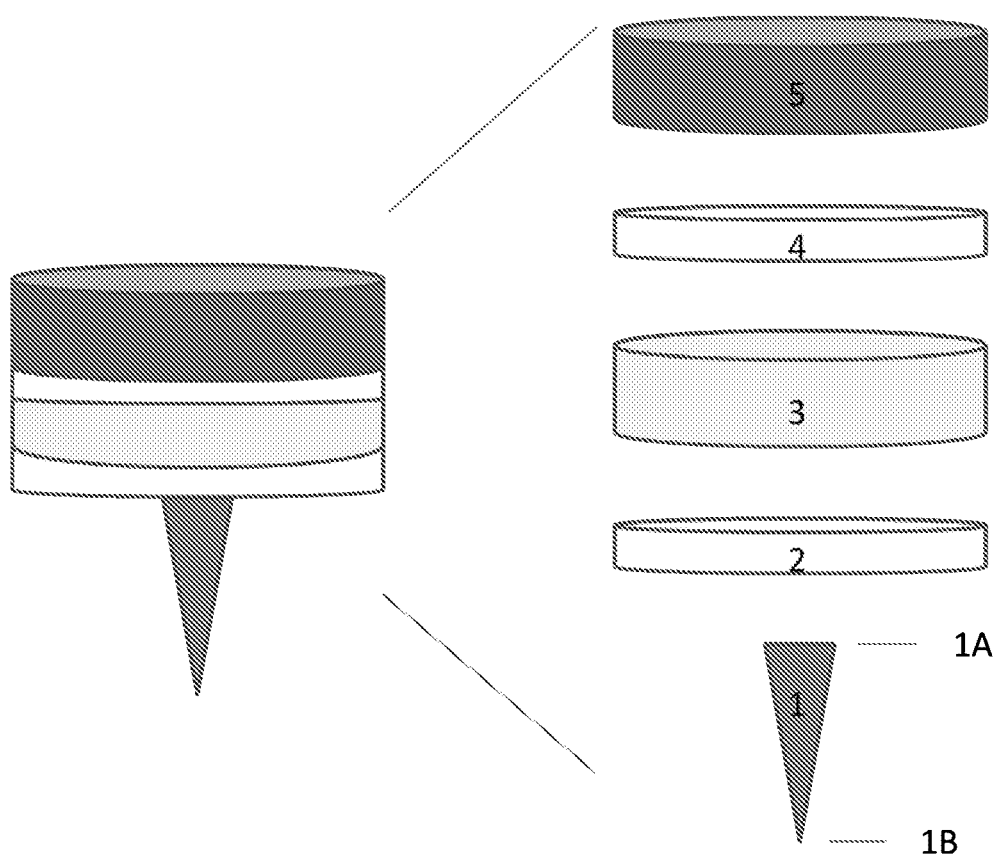

FIG. 3 illustrates a side view of the detection device of FIG. 3 in which 1 is a support member that contains at least one plant pathogen chemoattractant, the support member having two ends, 1A and 1B, 2 is a first filter comprising pores, 3 is a first culture medium, 4 is a second filter comprising pores and 5 is a second culture medium comprising at least one plant pathogen chemoattractant and a detection means. The detection means can optionally be a pH indicator.

Figure 4:
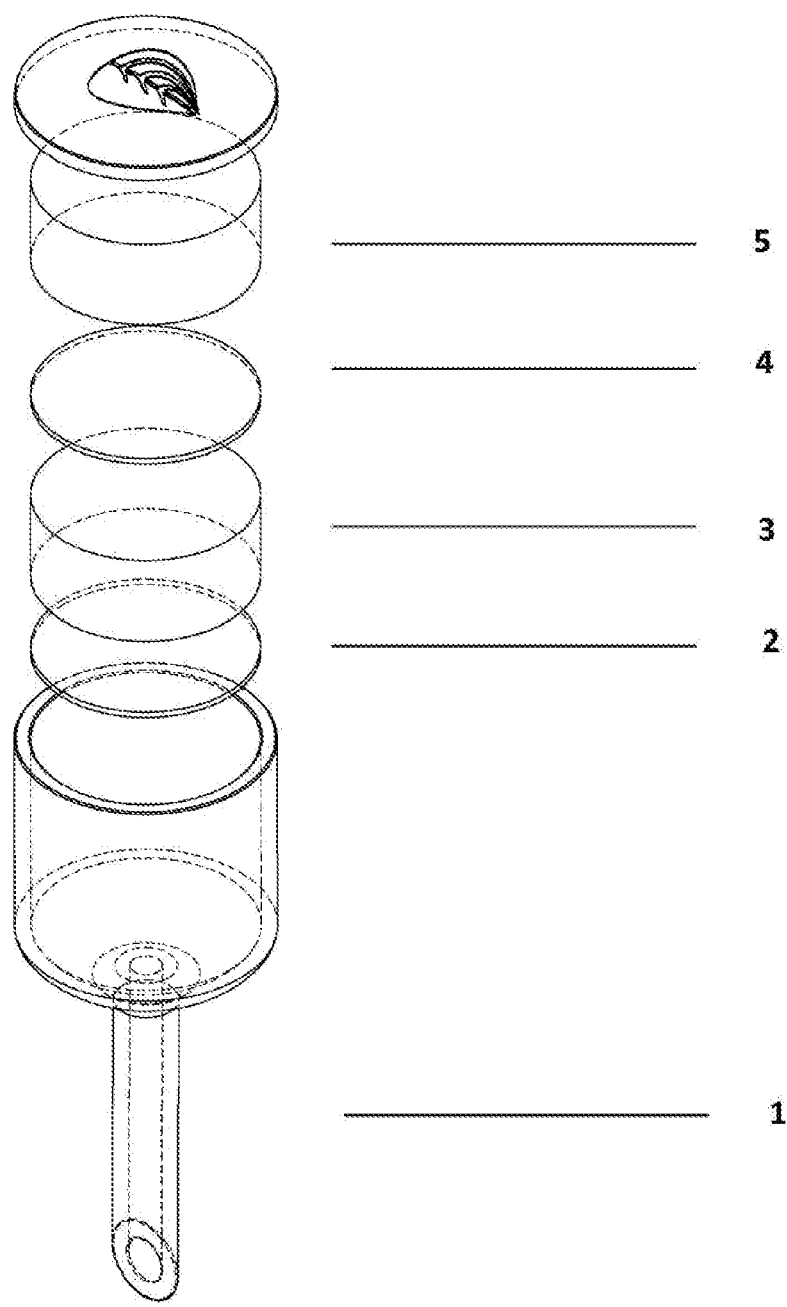

FIG. 4 illustrates a three-dimensional representation of the detection device of FIG. 3 in which 1 is a support member that contains at least one plant pathogen chemoattractant, 2 is a first filter comprising pores, 3 is a first culture medium, 4 is a second filter comprising pores and 5 is a second culture medium comprising at least one plant pathogen chemoattractant and a detection means. The detection means can optionally be a pH indicator.

Figure 5:
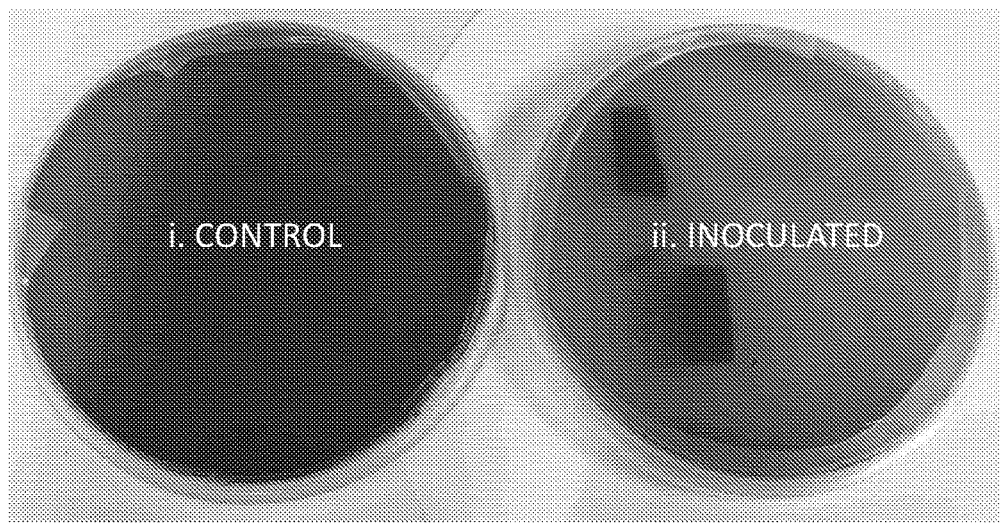
Figure 5:
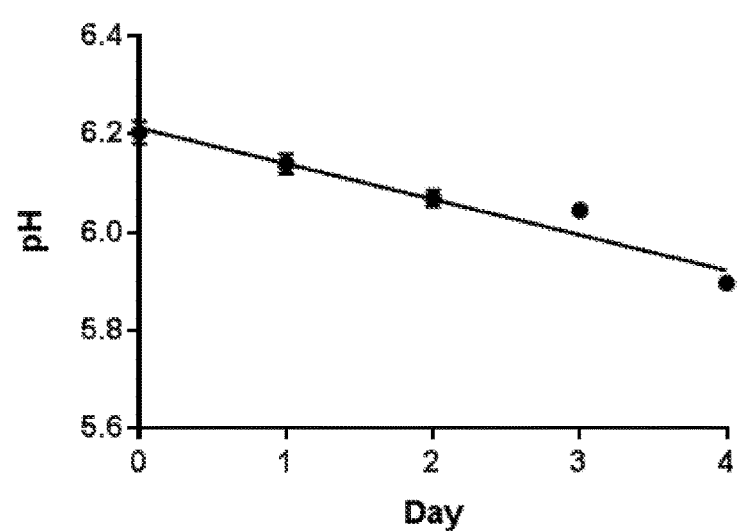

FIG. 5 A) Picture representing the colour change of the device after the addition of *Phytophthora*. i) Device without inoculation with *Phytophthora infestans* ii) Device after the inoculation with *Phytophthora* (picture taken 96 hours after inoculation (Day 4)). B) Graph depicting the pH change over 4 days after the inoculation of the media growth plates with *Phytophthora infestans*. Values are averages of 3 repeats, and error bars are standard deviation.

In a preferred embodiment the device detects spores from the plant pathogen *Phytophthora*. In one embodiment, the plant pathogen chemoattractant is a chemoattractant for one or more species of *Phytophthora*. In one embodiment, the at least one plant pathogen chemoattractant attracts multiple plant pathogens, including at least one species of *Phytophthora*. As used herein, the term "*Phytophthora*" includes all the species of the genus *Phytophthora*. The species of *Phytophthora* detected can include any of *Phytophthora taxon Agathis, Phytophthora alni, Phytophthora boehmeriae, Phytophthora botryose, ibrassicae, Phytophthora cactorum, Phytophthora cajani, Phytophthora cambivora, Phytophthora capsici, Phytophthora cinnamomi, Phytophthora citricola, Phytophthora citrophthora, Phytophthora clandestine, Phytophthora colocasiae, Phytophthora cryptogea, Phytophthora drechsleri, Phytophthora diwan ackerman, Phytophthora erythroseptica, Phytophthora fragariae, Phytophthora fragariae var. rubi, Phytophthora Gemini, Phytophthora glovera, Phytophthora gonapodyides, Phytophthora heveae, Phytophthora hibernalis, Phytophthora humicola, Phytophthora hydropathical, Phytophthora irrigate, Phytophthora idaei, Phytophthora ilicis, Phytophthora infestans, Phytophthora inflate, Phytophthora ipomoeae, Phytophthora iranica, Phytophthora katsurae, Phytophthora kernoviae, Phytophthora lateralis, Phytophthora medicaginis, Phytophthora megakarya, Phytophthora megasperma, Phytophthora melonis, Phytophthora mirabilis, Phytophthora multivesiculata, Phytophthora nemorosa, Phytophthora nicotianae, Phytophthora PaniaKara, Phytophthora palmivora, Phytophthora phaseoli, Phytophthora pini, Phytophthora porri, Phytophthora plurivora, Phytophthora primulae, Phytophthora pseudosyringae, Phytophthora pseudotsugae, Phytophthora quercina, Phytophthora ramorum, Phytophthora sinensis, Phytophthora sojae, Phytophthora syringae, Phytophthora tentaculata, Phytophthora trifolii* or *Phytophthora vignae*. In a particularly preferred embodiment, the device detects zoospores from the plant pathogen *Phytophthora*.

In an alternative embodiment, the device detects spores from the plant pathogen *Magnaporthe*. In one embodiment, the plant pathogen chemoattractant is a chemoattractant for one or more species of *Magnaporthe*. In one embodiment, the at least one plant pathogen chemoattractant attracts multiple plant pathogens, including at least one species of *Magnaporthe*. As used herein, the term "*Magnaporthe*" includes all the species of the genus *Magnaporthe*. The species of *Magnaporthe* detected can include any of *Magnaporthe oryzae, Magnaporthe grisea, Magnaporthe poae, Magnaporthe rhizophila* or *Magnaporthe salvinii*.

In another embodiment, the device detects spores from the plant pathogen *Botrytis*. In one embodiment, the plant pathogen chemoattractant is a chemoattractant for one or more species of *Botrytis*. In one embodiment, the at least one plant pathogen chemoattractant attracts multiple plant pathogens, including at least one species of *Botrytis*. As used herein, the term "*Botrytis*" includes all the species of the genus *Botrytis*. The species of *Botrytis* detected can include *Botrytis cinerea*.

In another embodiment, the device detects spores from the plant pathogen *Cochiliobolus*. In one embodiment, the plant pathogen chemoattractant is a chemoattractant for one or more species of *Cochiliobolus*. In one embodiment, the at least one plant pathogen chemoattractant attracts multiple plant pathogens, including at least one species of *Cochiliobolus*. As used herein, the term "*Cochiliobolus*" includes all the species of the genus *Cochiliobolus*. The species of *Cochiliobolus* detected can include *Cochiliobolus carbonum, Cochiliobolus victoriae* or *Cochiliobolus sativus*.

In another embodiment, the device detects spores from the plant pathogen *Puccinia*. In one embodiment, the plant pathogen chemoattractant is a chemoattractant for one or more species of *Puccinia*. In one embodiment, the at least one plant pathogen chemoattractant attracts multiple plant pathogens, including at least one species of *Puccinia*. As used herein, the term "*Puccinia*" includes all the species of the genus *Puccinia*. The species of *Puccinia* detected can include any of *Puccinia persistens, Puccinia graminis, Puccinia sorghi, Puccinia polysora, Puccinia kuehnil* or *Puccinia melanocephala*.

In an alternative embodiment, the device detects spores from the plant pathogen *Uromyces*. In one embodiment, the plant pathogen chemoattractant is a chemoattractant for one or more species of *Uromyces*. In one embodiment, the at least one plant pathogen chemoattractant attracts multiple plant pathogens, including at least one species of *Uromyces*. As used herein, the term "*Uromyces*" includes all the species of the genus *Uromyces*. The species of *Uromyces* detected can include any of *Uromyces appendiculatus* and *Uromyces phaseoli*.

In an alternative embodiment, the device detects spores from the plant pathogen *Gymnosporangium*. In one embodiment, the plant pathogen chemoattractant is a chemoattractant for one or more species of *Gymnosporangium*. In one embodiment, the at least one plant pathogen chemoattractant attracts multiple plant pathogens, including at least one species of *Gymnosporangium*. As used herein, the term "*Gymnosporangium*" includes all the species of the genus *Gymnosporangium*. The species of *Gymnosporangium* detected can include *Gymnosporangium juniperi-virginainae*.

In an alternative embodiment, the device detects spores from the plant pathogen *Hemileia*. In one embodiment, the plant pathogen chemoattractant is a chemoattractant for one or more species of *Hemileia*. In one embodiment, the at least one plant pathogen chemoattractant attracts multiple plant pathogens, including at least one species of *Hemileia*. As used herein, the term "*Hemileia*" includes all the species of the genus *Hemileia*. The species of *Hemileia* detected can include *Hemileia vastatrix*.

In an alternative embodiment, the device detects spores from the plant pathogen *Fusarium*. In one embodiment, the plant pathogen chemoattractant is a chemoattractant for one or more species of *Fusarium*. In one embodiment, the at least one plant pathogen chemoattractant attracts multiple plant pathogens, including at least one species of *Fusarium*. As used herein, the term "*Fusarium*" includes all the species of the genus *Fusarium*. The species of *Fusarium* detected can include *Fusarium graminearum, Fusarium oxysporum, Fusarium avenaceum, Fusarium culmorum, Fusarium equiseti, Fusarium poae, Fusarium sacchari, Fusarium moniliforme, Fusarium fujikuroi, Fusarium decemcellulare, Fusarium manginifera, Fusarium pallidoroseum, Fusarium episphaeria, Fusarium lateritium, Fusarium nivale, Fusarium rigidiuscula, Fusarium dimerum, Fusarium merismoides, Fusarium anthophilum, Fusarium circinatum, Fusarium proliferatum, Fusarium subglutinans, Fusarium thapsinum, Fusarium verticillioides, Fusarium roseum, Fusarium solani, Fusarium tricinctum, Fusarium acuminatum, Fusarium armeniacum, Fusarium compactum, Fusarium crookwellense, Fusarium longipe, Fusarium heterosporum, Fusarium polyphialidicum, Fusarium pseudograminearum, Fusarium semitectum, Fusarium torulosum, Fusarium chlamydosporum, Fusarium sporotrichioides, Fusarium clamidosporium, Fusarium nelsonii, Fusarium nygamai, Fusarium pseudonygamai, Fusarium andiyazi, Fusarium aywerte, Fusarium babinda, Fusarium beomiforme, Fusarium camptoceras, Fusarium hostae, Fusarium konzum, Fusarium musarum, Fusarium napiforme, Fusarium nurragi, Fusarium redolens, Fusarium sambucinum, Fusarium scirpi, Fusarium acutatum, Fusarium bactridioides, Fusarium begoniae, Fusarium brevicatenulatum, Fusarium bulbicola, Fusarium denticulatum, Fusarium dlaminii, Fusarium fractiflexum, Fusarium globosum, Fusarium guttiforme, Fusariumlactis, Fusarium mangiferae, Fusarium phyllophilum; Fusarium pseudoanthophilum; Fusarium pseudocircinatum; Fusarium ramigenum, Fusarium sterilihyphosum, Fusarium succisae, Fusarium udum, Fusarium cerealis, Fusarium crookwellense, Fusariumlunulosporum, Fusarium commune, Fusarium miscanthi, Fusarium phaseol, Fusarium tucumaniae, Fusarium virguliforme, Fusarium sporotrichoides, Fusarium bubigeum, Fusarium langsethiae, Fusarium Lycopersici* or *Fusarium sulphureum.*

In an alternative embodiment, the device detects spores from the plant pathogen *Gibberella*. In one embodiment, the plant pathogen chemoattractant is a chemoattractant for one or more species of *Gibberella*. In one embodiment, the at least one plant pathogen chemoattractant attracts multiple plant pathogens, including at least one species of *Gibberella*. As used herein, the term "*Gibberella*" includes all the species of the genus *Gibberella*. The species of *Gibberella* detected can include any of *Gibberella zeae, Gibberella cyanogena, Gibberella intricans, Gibberella avenacea* or *Gibberella fujikuroi.*

In an alternative embodiment, the device detects spores from the plant pathogen *Blumeria*. In one embodiment, the plant pathogen chemoattractant is a chemoattractant for one or more species of *Blumeria*. In one embodiment, the at least one plant pathogen chemoattractant attracts multiple plant pathogens, including at least one species of *Blumeria*. As used herein, the term "*Blumeria*" includes all the species of the genus *Blumeria*. The species of *Blumeria* detected can include *Blumeria graminis.*

In an alternative embodiment, the device detects spores from the plant pathogen *Mycosphaerella*. In one embodiment, the plant pathogen chemoattractant is a chemoattractant for one or more species of *Mycosphaerella*. In one embodiment, the at least one plant pathogen chemoattractant attracts multiple plant pathogens, including at least one species of *Mycosphaerella*. As used herein, the term "*Mycosphaerella*" includes all the species of the genus *Mycosphaerella*. The species of *Mycosphaerella* detected can include any of *Mycosphaerella angulata Mycosphaerella tassiana, Mycosphaerella zeae-maydis, Mycosphaerella ellipsoidea, Mycosphaerella irregulariramosa, Mycosphaerella juvenis, Mycosphaerella lateralis, Mycosphaerella marksii, Mycosphaerella nubilosa, Mycosphaerella fori, Mycosphaerella musicola, Mycosphaerella fijiensis, Mycosphaerella effigurata, Mycosphaerella fraxinicola, Mycosphaerella juglandis, Mycosphaerella fragariae, Mycosphaerella pinodes, Mycosphaerella graminicola, Mycosphaerella gossypina, Mycosphaerella holci, Mycosphaerella killiani, Mycosphaerella brassicicola, Mycosphaerella capsellae, Mycosphaerella vaccina, Mycosphaerella citrullina, Mycosphaerella arbuticola, Mycosphaerella melonis, Mycosphaerella scaevolae, Mycosphaerella pini, Mycosphaerella caricae, Mycosphaerella lythracearum, Mycosphaerella wolf, Mycosphaerella citri, Mycosphaerella pinodes, Mycosphaerella aurantia* sp. nov., *Mycosphaerella deamessii, Mycosphaerella pittospori, Mycosphaerella Septoria tritici* or *Mycosphaerella tassiana.*

In an alternative embodiment, the device detects spores from the plant pathogen *Colletotrichum*. In one embodiment, the plant pathogen chemoattractant is a chemoattractant for one or more species of *Colletotrichum*. In one embodiment, the at least one plant pathogen chemoattractant attracts multiple plant pathogens, including at least one species of *Colletotrichum*. As used herein, the term "*Colletotrichum*" includes all the species of the genus *Colletotrichum.*

In an alternative embodiment, the device detects spores from the plant pathogen *Sphacelotheca*. In one embodiment, the plant pathogen chemoattractant is a chemoattractant for one or more species of *Sphacelotheca*. In one embodiment, the at least one plant pathogen chemoattractant attracts multiple plant pathogens, including at least one species of *Sphacelotheca*. As used herein, the term "*Sphacelotheca*" includes all the species of the *Sphacelotheca*. The species of *Sphacelotheca* detected can include *Sphacelotheca reiliana.*

In an alternative embodiment, the device detects spores from the plant pathogen *Sporisorium*. In one embodiment, the plant pathogen chemoattractant is a chemoattractant for one or more species of *Sporisorium*. In one embodiment, the at least one plant pathogen chemoattractant attracts multiple plant pathogens, including at least one species of *Sporisorium*. As used herein, the term "*Sporisorium*" includes all the species of the *Sporisorium*. The species of *Sporisorium* detected can include *Sporisorium holci-sorghi.*

In an alternative embodiment, the device detects spores from the plant pathogen *Ustilaginoidea*. In one embodiment, the plant pathogen chemoattractant is a chemoattractant for one or more species of *Ustilaginoidea*. In one embodiment, the at least one plant pathogen chemoattractant attracts multiple plant pathogens, including at least one species of *Ustilaginoidea*. As used herein, the term "*Ustilaginoidea*" includes all the species of the *Ustilaginoidea*. The species of *Ustilaginoidea* detected can include *Ustilaginoidea virens.*

In an alternative embodiment, the device detects spores from the plant pathogen *Ustilago*. In one embodiment, the plant pathogen chemoattractant is a chemoattractant for one or more species of *Ustilago*. In one embodiment, the at least one plant pathogen chemoattractant attracts multiple plant pathogens, including at least one species of *Ustilago*. As used herein, the term "*Ustilago*" includes all the species of the *Ustilago*. The species of *Ustilago* detected can include any of *Ustilago zeae* or *Ustilago maydis*.

In an alternative embodiment, the device detects spores from the plant pathogen *Melampsora* In one embodiment, the plant pathogen chemoattractant is a chemoattractant for one or more species of *Melampsora*. In one embodiment, the at least one plant pathogen chemoattractant attracts multiple plant pathogens, including at least one species of *Melampsora*. As used herein, the term "*Melampsora*" includes all the species of the *Melampsora*. The species of *Melampsora* detected can include any of *Melampsora medusae*, *Melampsora lini* or *Melampsora occidentalis*.

In an alternative embodiment, the device detects spores from the plant pathogen *Pythium*. In one embodiment, the plant pathogen chemoattractant is a chemoattractant for one or more species of *Pythium*. In one embodiment, the at least one plant pathogen chemoattractant attracts multiple plant pathogens, including at least one species of *Pythium*. As used herein, the term "*Pythium*" includes all the species of the *Pythium*. The species of *Pythium* detected can include any of *Pythium zeae, Pythium acanthicum, Pythium acanthophoron, Pythium acrogynum, Pythium adhaerens, Pythium amasculinum, Pythium anandrum, Pythium angustatum, Pythium aphanidermatum, Pythium apleroticum, Pythium aquatile, Pythium aristosporum, Pythium arrhenomanes, Pythium attrantheridium, Pythium bifurcatum, Pythium boreale, Pythium buismaniae, Pythium butleri, Pythium campanulatum, Pythium canariense, Pythium capillosum, Pythium carbonicum, Pythium carolinianum, Pythium catenulatum, Pythium chamaehyphon, Pythium chondricola, Pythium citrinum, Pythium coloratum, Pythium conidiophorum, Pythium Pythium contiguanum, Pythium cryptoirregulare, Pythium cucurbitacearum, Pythium cylindrosporum, Pythium cystogenes, Pythium debaryanum, Pythium deliense, Pythium destruens, Pythium diclinum, Pythium dimorphum, Pythium dissimile, Pythium dissotocum, Pythium echinulatum, Pythium erinaceum, Pythium flevoense, Pythium folliculosum, Pythium glomeratum, Pythium graminicola, Pythium grandisporangium, Pythium guiyangense, Pythium helicandrum, Pythium Pythium helicoides, Pythium heterothallicum, Pythium hydnosporum, Pythium hypogynum, Pythium indigoferae, Pythium inflatum, Pythium insidiosum, Pythium ntermedium, Pythium irregulare, Pythium iwayamae, Pythium jasmonium, Pythium kunmingense, Pythium litorale, Pythium longandrum, Pythium ongisporangium, Pythium lutarium, Pythium macrosporum, Pythium mamillatum, Pythium marinum, Pythium marsipium, Pythium mastophorum, Pythium egacarpum, Pythium megalacanthum, Pythium middletonii, Pythium minus, Pythium monospermum, Pythium montanum, Pythium multisporum, Pythium myriotylum, Pythium nagaii, Pythium nodosum, Pythium nunn, Pythium oedochilum, Pythium nunn okanoganense, Pythium nunn oligandrum, Pythium ornacarpum, Pythium orthogonon, Pythium ostracodes, Pythium pachycaule, Pythium pachycaule, Pythium paddicum, Pythium paroecandrum, Pythium parvum, Pythium ectinolyticum, Pythium periilum, Pythium periplocum, Pythium perniciosum, Pythium perplexum, Pythium phragmitis, Pythium pleroticum, Pythium plurisporium, Pythium polymastum, Pythium porphyrae, Pythium prolatum, Pythium proliferatum, Pythium pulchrum, Pythium pyrilobum, Pythium quercum, Pythium radiosum, Pythium ramificatum, Pythium regulare, Pythium rhizo-oryzae, Pythium rhizosaccharum, Pythium rostratifingens, Pythium rostratum, salpingophorum, Pythium scieroteichum, Pythium segnitium, Pythium spiculum, Pythium spinosum, Pythium splendens, Pythium sterilum, Pythium stipitatum, Pythium sulcatum, sylvaticum, Pythium terrestris, Pythium orulosum, Pythium tracheiphilum, Pythium ultimum, Pythium ultimurn* var. *ultimum, Pythium uncinulatum, Pythium undulatum, Pythium vanterpoolii, Pythium vexans, Pythium viniferum, Pythium violae, Pythium volutum, Pythium zingiberis* or *Pythium zingiberum*.

In an alternative embodiment, the device detects spores from the plant pathogen *Achyla*. In one embodiment, the plant pathogen chemoattractant is a chemoattractant for one or more species of *Achyla*. In one embodiment, the at least one plant pathogen chemoattractant attracts multiple plant pathogens, including at least one species of *Achyla*. As used herein, the term "*Achyla*" includes all the species of the *Achyla*. The species of Achy/a detected can include any of *Achyla, ambisexualis, Achyla ambispora, Achyla apiculata, Achyla bisexualis, Achyla colorate, Achyla conspicua, Achyla klebsiana, Achyla oblongata, Achyla racemose* or *Achyla treleaseana*.

In an alternative embodiment, the device detects spores from the plant pathogen *Aphanomyces*. In one embodiment, the plant pathogen chemoattractant is a chemoattractant for one or more species of *Aphanomyces*. In one embodiment, the at least one plant pathogen chemoattractant attracts multiple plant pathogens, including at least one species of *Aphanomyces*. As used herein, the term "*Aphanomyces*" includes all the species of the *Aphanomyces*. The species of *Aphanomyces* detected can include any of *Aphanomyces acinetophagus, Aphanomyces americanus, Aphanomyces amphigynus, Aphanomyces Aphanomyces apophysii, Aphanomyces astaci, Aphanomyces balboensis, Aphanomyces bosminae, Aphanomyces brassicae, Aphanomyces camptostylus, Aphanomyces cladogamus, Aphanomyces cochlioides, Aphanomyces coniger, Aphanomyces daphniae, Aphanomyces euteiches, Aphanomyces exoparasiticus, Aphanomyces rigidophilus, Aphanomyces gordejevi, Aphanomyces helicoides, Aphanomyces hydatinae, Aphanomyces iridis, Aphanomyces irregularis, Aphanomyces keratinophilus, Aphanomyces laevis, Aphanomyces magnusii, Aphanomyces norvegicus, Aphanomyces ovidestruens, Aphanomyces parasiticus, Aphanomyces patersonii, Aphanomyces phycophilus, Aphanomyces pisci, Aphanomyces piscicida, Aphanomyces polysporis, Aphanomyces raphani, Aphanomyces salsuginosus, Aphanomyces scaber, Aphanomyces sparrowii, Aphanomyces stellatus,* or *Aphanomyces volgensis*.

In an alternative embodiment, the device detects spores from the plant pathogen *Albugo*. In one embodiment, the plant pathogen chemoattractant is a chemoattractant for one or more species of *Albugo*. In one embodiment, the at least one plant pathogen chemoattractant attracts multiple plant pathogens, including at least one species of *Albugo*. As used herein, the term "*Albugo*" includes all the species of the *Albugo*. The species of *Albugo* detected can include any of *Albugo bliti, Albugo candida, Albugo ipmoeae-panduratae, Albugo laibachii, Albugo occidentalis* or *Albugo tragopogonis*.

In an alternative embodiment, the device detects spores from the plant pathogen *Wilsoniana*. In one embodiment, the plant pathogen chemoattractant is a chemoattractant for one or more species of *Wilsoniana*. In one embodiment, the at least one plant pathogen chemoattractant attracts multiple plant pathogens, including at least one species of *Wilsoniana*. As used herein, the term "*Wilsoniana*" includes all the species of the *Wilsoniana*. The species of *Wilsoniana* detected can include any of *Wilsoniana platensis* or *Wilsoniana portulacae*.

In an alternative embodiment, the device detects spores from the plant pathogen *Basidiophora*. In one embodiment, the plant pathogen chemoattractant is a chemoattractant for one or more species of *Basidiophora*. In one embodiment, the at least one plant pathogen chemoattractant attracts multiple plant pathogens, including at least one species of *Basidiophora*. As used herein, the term "*Basidiophora*" includes all the species of the *Basidiophora*. The species of *Basidiophora* detected can include any of *Basidiophora entospora*, *Basidiophora simplex* or *Basidiophora kellermannii*.

In an alternative embodiment, the device detects spores from the plant pathogen *Bremia*. In one embodiment, the plant pathogen chemoattractant is a chemoattractant for one or more species of *Bremia*. In one embodiment, the at least one plant pathogen chemoattractant attracts multiple plant pathogens, including at least one species of *Bremia*. As used herein, the term "*Bremia*" includes all the species of the *Bremia*. The species of *Bremia* detected can include any of *Bremia graminicola* or *Bremia lactucae*.

In an alternative embodiment, the device detects spores from the plant pathogen *Alternaria*. As used herein, the term "*Alternaria*" includes all the species of the *Alternaria*. In one embodiment, the plant pathogen chemoattractant is a chemoattractant for one or more species of *Alternaria*. In one embodiment, the at least one plant pathogen chemoattractant attracts multiple plant pathogens, including at least one species of *Alternaria*. The species of *Alternaria* detected can include any of *Alternaria alternata*, *Alternaria alternantherae*, *Alternaria arborescens*, *Alternaria arbusti*, *Alternaria blumeae*, *Alternaria brassicae*, *Alternaria brassicicola*, *Alternaria burnsii*, *Alternaria carotiincultae*, *Alternaria carthami*, *Alternaria celosiae*, *Alternaria cinerariae*, *Alternaria citri*, *Alternaria conjuncta*, *Alternaria cucumerina*, *Alternaria dauci*, *Alternaria dianthi*, *Alternaria dianthicola*, *Alternaria eichhorniae*, *Alternaria euphorbiicola*, *Alternaria gaisen*, *Alternaria helianthi*, *Alternaria helianthicola*, *Alternaria hungarica*, *Alternaria infectoria*, *Alternaria japonica*, *Alternaria limicola*, *Alternaria linicola*, *Alternaria longipes*, *Alternaria molesta*, *Alternaria panax*, *Alternaria perpunctulata*, *Alternaria petroselini*, *Alternaria radicina*, *Alternaria raphani*, *Alternaria saponariae*, *Alternaria selini*, *Alternaria senecionis*, *Alternaria solani*, *Alternaria smyrnii*, *Alternaria tenuissima*, *Alternaria triticina*, *Alternaria Lycopersici* or *Alternaria zinniae*.

In an alternative embodiment, the device detects spores from the plant pathogen *Pseudopezicula*. In one embodiment, the plant pathogen chemoattractant is a chemoattractant for one or more species of *Pseudopezicula*. In one embodiment, the at least one plant pathogen chemoattractant attracts multiple plant pathogens, including at least one species of *Pseudopezicula*. As used herein, the term "*Pseudopezicula*" includes all the species of the *Pseudopezicula*. The species of *Pseudopezicula* detected can include any of *Pseudopezicula tetraspora* or *Pseudopezicula tracheiphila*.

In an alternative embodiment, the device detects spores from the plant pathogen *Cercospora*. In one embodiment, the plant pathogen chemoattractant is a chemoattractant for one or more species of *Cercospora*. In one embodiment, the at least one plant pathogen chemoattractant attracts multiple plant pathogens, including at least one species of *Cercospora*. As used herein, the term "*Cercospora*" includes all the species of the *Cercospora*. The species of *Pseudopezicula* detected can include any of *Cercospora acetosella*, *Cercospora aciculina*, *Cercospora agerati*, *Cercospora alabemensis*, *Cercospora alismatis*, *Cercospora althaeina*, *Cercospora angreci*, *Cercospora angulata*, *Cercospora apii*, *Cercospora apii* fsp. *Cercospora clerodendri*, *Cercospora apiicola*, *Cercospora arachidicola*, *Cercospora arctii*, *Cercospora arctii-ambrosiae*, *Cercospora asparagi*, *Cercospora atro-marginalis*, *Cercospora atrofiliformis*, *Cercospora beticola*, *Cercospora bolleana*, *Cercospora bougainvilleae*, *Cercospora brachiata*, *Cercospora byliana*, *Cercospora brachypus*, *Cercospora brassicicola*, *Cercospora brunkii*, *Cercospora bunchosiae*, *Cercospora canescens*, *Cercospora cannabis*, *Cercospora cantuariensis*, *Cercospora capsici*, *Cercospora caribaea*, *Cercospora carotae*, *Cercospora circumscissa*, *Cercospora citrullina*, *Cercospora clemensiae*, *Cercospora coffeicola*, *Cercospora coryli*, *Cercospora corylina*, *Cercospora fragariae*, *Cercospora fuchsiae*, *Cercospora fusca*, *Cercospora fusimaculans*, *Cercospora gerberae*, *Cercospora halstedii*, *Cercospora handelii*, *Cercospora hayi*, *Cercospora hydrangeae*, *Cercospora kaki*, *Cercospora kikuchii*, *Cercospora lentis*, *Cercospora liquidambaris*, *Cercospora longipes*, *Cercospora sugarcane*, *Cercospora longissima*, *Cercospora mamaonis*, *Cercospora mangiferae*, *Cercospora medicaginis*, *Cercospora melongenae*, *Cercospora minima*, *Cercospora minuta*, *Cercospora musae*, *Cercospora nicotianae*, *Cercospora odontoglossi*, *Cercospora oryzae*, *Cercospora papayae*, *Cercospora penniseti*, *Cercospora pisasativae*, *Cercospora platanicola*, *Cercospora puderii*, *Cercospora pulcherrima*, *Cercospora rhapidicola*, *Cercospora rosicola*, *Cercospora rubrotincta*, *Cercospora sojina*, *Cercospora solani*, *Cercospora solani-tuberosi*, *Cercospora sorghi*, *Cercospora theae*, *Cercospora tuberculans*, *Cercospora vexans*, *Cercospora vicosae*, *Cercospora zeae-maydis*, *Cercospora zebrina*, *Cercospora zonata* or *Cercospora personata*.

In an alternative embodiment, the device detects spores from the plant pathogen *Elsinoë*. In one embodiment, the plant pathogen chemoattractant is a chemoattractant for one or more species of *Elsinoë*. In one embodiment, the at least one plant pathogen chemoattractant attracts multiple plant pathogens, including at least one species of *Elsinoë*. As used herein, the term "*Elsinoë*" includes all the species of the *Elsinoë*. The species of *Elsinoë* detected can include any of *Elsinoë ampelina*, *Elsinoëaustralis*, *Elsinoëbatatas*, *Elsinoëbrasiliensis*, *Elsinoëfawcettii*, *Elsinoë leucospila*, *Elsinoë mangiferae*, *Elsinoë pyri*, *Elsinoë randii*, *Elsinoë rosarum*, *Elsinoë sacchari*, *Elsinoë theae* or *Elsinoë veneta*.

In an alternative embodiment, the device detects spores from the plant pathogen *Sphaceloma ampelinum*. In one embodiment, the plant pathogen chemoattractant is a chemoattractant for one or more species of *Sphaceloma ampelinum*. In one embodiment, the at least one plant pathogen chemoattractant attracts multiple plant pathogens, including at least one species of *Sphaceloma ampelinum*. As used herein, the term "*Sphaceloma ampelinum*" includes all the species of the *Sphaceloma ampelinum*. The species of *Sphaceloma ampelinum* detected can include any of *Sphaceloma ampelinum arachidis*, *Sphaceloma ampelinum coryli*, *Sphaceloma ampelinum menthae*, *Sphaceloma ampelinum perseae*, *Sphaceloma ampelinum poinsettiae*, *Sphaceloma ampelinum pyrinum*, *Sphaceloma ampelinum andii*, s *Sphaceloma ampelinum acchari* or *Sphaceloma ampelinum* these.

In an alternative embodiment, the device detects spores from the plant pathogen *Armillaria mellea*. In one embodiment, the plant pathogen chemoattractant is a chemoattractant for one or more species of *Armillaria mellea*. In one embodiment, the at least one plant pathogen chemoattractant attracts multiple plant pathogens, including at least one species of *Armillaria mellea*. As used herein, the term "*Armillaria mellea*" includes all the species of the *Armillaria mellea*.

In an alternative embodiment, the device detects spores from the plant pathogen *Rhizomorpha subcorticalis*. In one embodiment, the plant pathogen chemoattractant is a chemoattractant for one or more species of *Rhizomorpha subcorticalis*. In one embodiment, the at least one plant pathogen chemoattractant attracts multiple plant pathogens, including at least one species of *Rhizomorpha subcorticalis*. As used herein, the term "*Rhizomorpha subcorticalis*" includes all the species of the *Rhizomorpha subcorticalis*.

In an alternative embodiment, the device detects spores from the plant pathogen *Diplocarpon*. In one embodiment, the plant pathogen chemoattractant is a chemoattractant for one or more species of *Diplocarpon*. In one embodiment, the at least one plant pathogen chemoattractant attracts multiple plant pathogens, including at least one species of *Diplocarpon*. As used herein, the term "*Diplocarpon*" includes all the species of the *Diplocarpon*. The species of *Diplocarpon* detected can include any of *Diplocarpon earlianum*, *Diplocarpon hymenaeae*, *Diplocarpon impessum*, *Diplocarpon mali*, *Diplocarpon mespili*, *Diplocarpon polygoni*, *Diplocarpon saponariae*, *Diplocarpon coprosmae*, *Diplocarpon graminea*, *Diplocarpon schoepfiae* or *Diplocarpon rosae*.

In an alternative embodiment, the device detects spores from the plant pathogen *Marssonia*. In one embodiment, the plant pathogen chemoattractant is a chemoattractant for one or more species of *Marssonia*. In one embodiment, the at least one plant pathogen chemoattractant attracts multiple plant pathogens, including at least one species of *Marssonia*. As used herein, the term "*Marssonia*" includes all the species of the *Marssonia*. The species of *Marssonia* detected can include *Marssonia rosae*.

In an alternative embodiment, the device detects spores from the plant pathogen *Uncinula*. In one embodiment, the plant pathogen chemoattractant is a chemoattractant for one or more species of *Uncinula*. In one embodiment, the at least one plant pathogen chemoattractant attracts multiple plant pathogens, including at least one species of *Uncinula*. As used herein, the term "*Uncinula*" includes all the species of the *Uncinula*. The species of *Uncinula* detected can include any of *Uncinula bicornis*, *Uncinula macrospora*, *Uncinula necator* or *Uncinula tulasnei*.

In an alternative embodiment, the device detects spores from the plant pathogen *Erysiphe*. In one embodiment, the plant pathogen chemoattractant is a chemoattractant for one or more species of *Erysiphe*. In one embodiment, the at least one plant pathogen chemoattractant attracts multiple plant pathogens, including at least one species of *Erysiphe*. As used herein, the term "*Erysiphe*" includes all the species of the *Erysiphe*. The species of *Erysiphe* detected can include any of *Erysiphe zeae*, *Erysiphe alphitoides*, *Erysiphe betae*, *Erysiphe brunneopunctata*, *Erysiphe cichoracearum*, *Erysiphe cruciferarum*, *Erysiphe fernandoae*, *Erysiphe flexuosa*, *Erysiphe graminis*, *Erysiphe heraclei*, *Erysiphe michikoae*, *Erysiphe necator* or *Erysiphe pisi*.

In an alternative embodiment, the device detects spores from the plant pathogen *Plasmopara*. In one embodiment, the plant pathogen chemoattractant is a chemoattractant for one or more species of *Plasmopara*. In one embodiment, the at least one plant pathogen chemoattractant attracts multiple plant pathogens, including at least one species of *Plasmopara*. As used herein, the term "*Plasmopara*" includes all the species of the *Plasmopara*. The species of *Plasmopara* detected can include any of *Plasmopara halstedii*, *Plasmopara nivea*, *Plasmopara obducens*, *Plasmopara viticola*, *Plasmopara helianthi* f. *helianthi*, *Plasmopara lactucaeradicis*, *Plasmopara penniseti* or *Plasmopara pygmaea*.

In an alternative embodiment, the device detects spores from the plant pathogen *Guignardia bidwellii*. In one embodiment, the plant pathogen chemoattractant is a chemoattractant for one or more species of *Guignardia*. In one embodiment, the at least one plant pathogen chemoattractant attracts multiple plant pathogens, including at least one species of *Guignardia*. As used herein, the term "*Guignardia bidwellii*" includes all the species of the *Guignardia bidwellii*.

In an alternative embodiment, the device detects spores from the plant pathogen *Colletotrichum*. In one embodiment, the plant pathogen chemoattractant is a chemoattractant for one or more species of *Colletotrichum*. In one embodiment, the at least one plant pathogen chemoattractant attracts multiple plant pathogens, including at least one species of *Colletotrichum*. As used herein, the term "*Colletotrichum*" includes all the species of the *Colletotrichum*. The species of *Colletotrichum* detected can include any of *Colletotrichum coffeanum*, *Colletotrichum coccodes*, *Colletotrichum graminicola* or *Colletotrichum dematium gloeosporioides*.

In an alternative embodiment, the device detects spores from the plant pathogen *Glomerella*. In one embodiment, the plant pathogen chemoattractant is a chemoattractant for one or more species of *Glomerella*. In one embodiment, the at least one plant pathogen chemoattractant attracts multiple plant pathogens, including at least one species of *Glomerella*. As used herein, the term "*Glomerella*" includes all the species of the *Glomerella*. The species of *Glomerella* detected can include any of *Glomerella* cingulate, *Glomerella tucumanensis* or *Glomerella falcatum*.

In an alternative embodiment, the device detects spores from the plant pathogen *Stemphylium*. In one embodiment, the plant pathogen chemoattractant is a chemoattractant for one or more species of *Stemphylium*. In one embodiment, the at least one plant pathogen chemoattractant attracts multiple plant pathogens, including at least one species of *Stemphylium*. As used herein, the term "*Stemphylium*" includes all the species of the *Stemphylium*. The species of *Stemphylium* detected can include any of *Stemphylium botryosum* or *Stemphylium herbarum*.

In an alternative embodiment, the device detects spores from the plant pathogen *Pleospora*. In one embodiment, the plant pathogen chemoattractant is a chemoattractant for one or more species of *Pleospora*. In one embodiment, the at least one plant pathogen chemoattractant attracts multiple plant pathogens, including at least one species of *Pleospora*. As used herein, the term "*Pleospora*" includes all the species of the *Pleospora*. The species of *Pleospora* detected can include any of *Pleospora tarda*, *Pleospora herbarum* or *Pleospora lycopersici*.

In an alternative embodiment, the device detects spores from the plant pathogen *Ulocladium*. In one embodiment, the plant pathogen chemoattractant is a chemoattractant for one or more species of *Ulocladium*. In one embodiment, the at least one plant pathogen chemoattractant attracts multiple plant pathogens, including at least one species of *Ulocladium*. As used herein, the term "*Ulocladium*" includes all the species of the *Ulocladium*. The species of *Ulocladium* detected can include *Ulocladium consortiale*.

In an alternative embodiment, the device detects spores from the plant pathogen *Stemphylium*. In one embodiment, the plant pathogen chemoattractant is a chemoattractant for one or more species of *Stemphylium*. In one embodiment, the at least one plant pathogen chemoattractant attracts multiple plant pathogens, including at least one species of *Stemphylium*. As used herein, the term "*Stemphylium*" includes all the species of the *Stemphylium*. The species of *Stemphylium* detected can include *Stemphylium consortiale*.

In an alternative embodiment, the device detects spores from the plant pathogen *Thielaviopsis*. In one embodiment, the plant pathogen chemoattractant is a chemoattractant for one or more species of *Thielaviopsis*. In one embodiment, the at least one plant pathogen chemoattractant attracts multiple plant pathogens, including at least one species of *Thielaviopsis*. As used herein, the term "*Thielaviopsis*" includes all the species of the *Thielaviopsis*. The species of *Thielaviopsis* detected can include *Thielaviopsis basicola*.

In an alternative embodiment, the device detects spores from the plant pathogen *Chalara*. In one embodiment, the plant pathogen chemoattractant is a chemoattractant for one or more species of *Chalara*. In one embodiment, the at least one plant pathogen chemoattractant attracts multiple plant pathogens, including at least one species of *Chalara*. As used herein, the term "*Chalara*" includes all the species of the *Chalara*. The species of *Chalara* detected can include any of *Chalara elegans*.

In an alternative embodiment, the device detects spores from the plant pathogen *Pseudocercospora*. In one embodiment, the plant pathogen chemoattractant is a chemoattractant for one or more species of *Pseudocercospora*. In one embodiment, the at least one plant pathogen chemoattractant attracts multiple plant pathogens, including at least one species of *Pseudocercospora*. As used herein, the term "*Pseudocercospora*" includes all the species of the *Pseudocercospora*. The species of *Pseudocercospora* detected can include *Pseudocercospora fuligena*.

In an alternative embodiment, the device detects spores from the plant pathogen *Macrophomina*. In one embodiment, the plant pathogen chemoattractant is a chemoattractant for one or more species of *Macrophomina*. In one embodiment, the at least one plant pathogen chemoattractant attracts multiple plant pathogens, including at least one species of *Macrophomina*. As used herein, the term "*Macrophomina*" includes all the species of the *Macrophomina*. The species of *Macrophomina* detected can include *Macrophomina Phaseolina*.

In an alternative embodiment, the device detects spores from the plant pathogen *Macrophoma*. In one embodiment, the plant pathogen chemoattractant is a chemoattractant for one or more species of *Macrophoma*. In one embodiment, the at least one plant pathogen chemoattractant attracts multiple plant pathogens, including at least one species of *Macrophoma*. As used herein, the term "*Macrophoma*" includes all the species of the *Macrophoma*. The species of *Macrophoma* detected can include *Macrophoma zeae*.

In an alternative embodiment, the device detects spores from the plant pathogen *Vaccinium*. In one embodiment, the plant pathogen chemoattractant is a chemoattractant for one or more species of *Vaccinium*. In one embodiment, the at least one plant pathogen chemoattractant attracts multiple plant pathogens, including at least one species of *Vaccinium*. As used herein, the term "*Vaccinium*" includes all the species of the *Vaccinium*. The species of *Vaccinium* detected can include *Vaccinium corymbosum*.

In an alternative embodiment, the device detects spores from the plant pathogen *Pyrenochaeta*. In one embodiment, the plant pathogen chemoattractant is a chemoattractant for one or more species of *Pyrenochaeta*. In one embodiment, the at least one plant pathogen chemoattractant attracts multiple plant pathogens, including at least one species of *Pyrenochaeta*. As used herein, the term "*Pyrenochaeta*" includes all the species of the *Pyrenochaeta*. The species of *Pyrenochaeta* detected can include *Pyrenochaeta lycopersici*.

In an alternative embodiment, the device detects spores from the plant pathogen *Didymella*. In one embodiment, the plant pathogen chemoattractant is a chemoattractant for one or more species of *Didymella*. In one embodiment, the at least one plant pathogen chemoattractant attracts multiple plant pathogens, including at least one species of *Didymella*. As used herein, the term "*Didymella*" includes all the species of the *Didymella*. The species of *Didymella* detected can include any of *Didymella lycopersici* or *Didymella exitalis*.

In an alternative embodiment, the device detects spores from the plant pathogen *Stemphylium*. In one embodiment, the plant pathogen chemoattractant is a chemoattractant for one or more species of *Stemphylium*. In one embodiment, the at least one plant pathogen chemoattractant attracts multiple plant pathogens, including at least one species of *Stemphylium*. As used herein, the term "*Stemphylium*" includes all the species of the *Stemphylium*. The species of *Stemphylium* detected can include any of *Stemphylium botryosum*, *Stemphylium lycopersici*, *Stemphylium loridanum* or *Stemphylium solani*.

In an alternative embodiment, the device detects spores from the plant pathogen *Botryotinia*. In one embodiment, the plant pathogen chemoattractant is a chemoattractant for one or more species of *Botryotinia*. In one embodiment, the at least one plant pathogen chemoattractant attracts multiple plant pathogens, including at least one species of *Botryotinia*. As used herein, the term "*Botryotinia*" includes all the species of the *Botryotinia*. The species of *Botryotinia* detected can include *Botryotinia fuckeliana*.

In an alternative embodiment, the device detects spores from the plant pathogen *Fulvia*. In one embodiment, the plant pathogen chemoattractant is a chemoattractant for one or more species of *Fulvia*. In one embodiment, the at least one plant pathogen chemoattractant attracts multiple plant pathogens, including at least one species of *Fulvia*. As used herein, the term "*Fulvia*" includes all the species of the *Fulvia*. The species of *Fulvia* detected can include *Fulvia fulva*.

In an alternative embodiment, the device detects spores from the plant pathogen *Mycovellosiella*. In one embodiment, the plant pathogen chemoattractant is a chemoattractant for one or more species of *Mycovellosiella*. In one embodiment, the at least one plant pathogen chemoattractant attracts multiple plant pathogens, including at least one species of *Mycovellosiella*. As used herein, the term "*Mycovellosiella*" includes all the species of the *Mycovellosiella*.

In an alternative embodiment, the device detects spores from the plant pathogen *Cladosporium*. In one embodiment, the plant pathogen chemoattractant is a chemoattractant for one or more species of *Cladosporium*. In one embodiment, the at least one plant pathogen chemoattractant attracts multiple plant pathogens, including at least one species of *Cladosporium*. As used herein, the term "*Cladosporium*" includes all the species of the *Cladosporium*. The species of *Cladosporium* detected can include any of *Cladosporium cladosporium*, *Cladosporium fulvum* or *Cladosporium herbarum*.

In an alternative embodiment, the device detects spores from the plant pathogen *Passalora*. In one embodiment, the plant pathogen chemoattractant is a chemoattractant for one or more species of *Passalora*. In one embodiment, the at least one plant pathogen chemoattractant attracts multiple plant pathogens, including at least one species of *Passalora*. As used herein, the term "*Passalora*" includes all the species of the *Passalora*. The species of *Passalora* detected can include *Passalora fulva*.

In an alternative embodiment, the device detects spores from the plant pathogen *Phoma*. In one embodiment, the plant pathogen chemoattractant is a chemoattractant for one or more species of *Phoma*. In one embodiment, the at least one plant pathogen chemoattractant attracts multiple plant pathogens, including at least one species of *Phoma*. As used herein, the term "*Phoma*" includes all the species of the *Phoma*. The species of *Phoma* detected can include *Phoma destructive*.

In an alternative embodiment, the device detects spores from the plant pathogen *Oidiopsis*. In one embodiment, the plant pathogen chemoattractant is a chemoattractant for one or more species of *Oidiopsis*. In one embodiment, the at least one plant pathogen chemoattractant attracts multiple plant pathogens, including at least one species of *Oidiopsis*. As used herein, the term "*Oidiopsis*" includes all the species of the *Oidiopsis*. The species of *Oidiopsis* detected can include *Oidiopsis sicula*.

In an alternative embodiment, the device detects spores from the plant pathogen *Leveillula*. In one embodiment, the plant pathogen chemoattractant is a chemoattractant for one or more species of *Leveillula*. In one embodiment, the at least one plant pathogen chemoattractant attracts multiple plant pathogens, including at least one species of *Leveillula*. As used herein, the term "*Leveillula*" includes all the species of the *Leveillula*. The species of *Leveillula* detected can include *Leveillula taurica*.

In an alternative embodiment, the device detects spores from the plant pathogen *Cochliobolus*. In one embodiment, the plant pathogen chemoattractant is a chemoattractant for one or more species of *Cochliobolus*. In one embodiment, the at least one plant pathogen chemoattractant attracts multiple plant pathogens, including at least one species of *Cochliobolus*. As used herein, the term "*Cochliobolus*" includes all the species of the *Cochliobolus*. The species of *Cochliobolus* detected can include *Cochliobolus heterostroophus*.

In an alternative embodiment, the device detects spores from the plant pathogen *Curvularia*. In one embodiment, the plant pathogen chemoattractant is a chemoattractant for one or more species of *Curvularia*. In one embodiment, the at least one plant pathogen chemoattractant attracts multiple plant pathogens, including at least one species of *Curvularia*. As used herein, the term "*Curvularia*" includes all the species of the *Curvularia*. The species of *Curvularia* detected can include any of *Curvularia clavate, Curvularia eragrostidis, Curvularia maculans, Curvularia hliobolus, Curvularia eragrostidis, Curvularia inaequalis, Curvularia intermedia, Cochliobolus intermedius, Curvularialunata, Curvularia Cochlioboluslunatus, Curvularia pallescens, Curvularia Cochliobolus pallescens, Curvularia senegalensis, Curvularia tuberculate*, or *Curvularia Cochliobolus tuberculatus*.

In an alternative embodiment, the device detects spores from the plant pathogen *Rhizoctonia*. In one embodiment, the plant pathogen chemoattractant is a chemoattractant for one or more species of *Rhizoctonia*. In one embodiment, the at least one plant pathogen chemoattractant attracts multiple plant pathogens, including at least one species of *Rhizoctonia*. As used herein, the term "*Rhizoctonia*" includes all the species of the *Rhizoctonia*. The species of *Rhizoctonia* detected can include *Rhizoctonia microsclerotia, Rhizoctonia solani* or *Rhizoctonia zeae*.

In an alternative embodiment, the device detects spores from the plant pathogen *bipolaris*. In one embodiment, the plant pathogen chemoattractant is a chemoattractant for one or more species of *bipolaris*. In one embodiment, the at least one plant pathogen chemoattractant attracts multiple plant pathogens, including at least one species of *bipolaris*. As used herein, the term "*bipolaris*" includes all the species of the *ipolaris*. The species of *bipolaris* detected can include *Bipolaris maydis*.

In an alternative embodiment, the device detects spores from the plant pathogen *Waitea*. In one embodiment, the plant pathogen chemoattractant is a chemoattractant for one or more species of *Waitea*. In one embodiment, the at least one plant pathogen chemoattractant attracts multiple plant pathogens, including at least one species of *Waitea*. As used herein, the term "*Waitea*" includes all the species of the *Waitea*. The species of *Waitea* detected can include *Waitea circinata*.

In an alternative embodiment, the device detects spores from the plant pathogen *Thanatephorus*. In one embodiment, the plant pathogen chemoattractant is a chemoattractant for one or more species of *Thanatephorus*. In one embodiment, the at least one plant pathogen chemoattractant attracts multiple plant pathogens, including at least one species of *Thanatephorus*. As used herein, the term "*Thanatephorus*" includes all the species of the *Thanatephorus*. The species of *Thanatephorus* detected can include *Thanatephorus cucumeris*.

In an alternative embodiment, the device detects spores from the plant pathogen *Corticium*. In one embodiment, the plant pathogen chemoattractant is a chemoattractant for one or more species of *Corticium*. In one embodiment, the at least one plant pathogen chemoattractant attracts multiple plant pathogens, including at least one species of *Corticium*. As used herein, the term "*Corticium*" includes all the species of the *Corticium*. The species of *Corticium* detected can include *Corticium sasakii*.

In an alternative embodiment, the device detects spores from the plant pathogen *Rhizopus*. In one embodiment, the plant pathogen chemoattractant is a chemoattractant for one or more species of *Rhizopus*. In one embodiment, the at least one plant pathogen chemoattractant attracts multiple plant pathogens, including at least one species of *Rhizopus*. As used herein, the term "*Rhizopus*" includes all the species of the *Rhizopus*. The species of *Rhizopus* detected can include *Rhizopus stolonifer, Rhizopus nigricans* or *Rhizopus arrhizus*.

In an alternative embodiment, the device detects spores from the plant pathogen *Septoria*. In one embodiment, the plant pathogen chemoattractant is a chemoattractant for one or more species of *Septoria*. In one embodiment, the at least one plant pathogen chemoattractant attracts multiple plant pathogens, including at least one species of *Septoria*. As used herein, the term "*Septoria*" includes all the species of the *Septoria*. The species of *Septoria* detected can include *Septoria lycopersici*.

In an alternative embodiment, the device detects spores from the plant pathogen *Geotrichum*. In one embodiment, the plant pathogen chemoattractant is a chemoattractant for one or more species of *Geotrichum*. In one embodiment, the at least one plant pathogen chemoattractant attracts multiple plant pathogens, including at least one species of *Geotrichum*. As used herein, the term "*Geotrichum*" includes all the species of the *Geotrichum*. The species of *Geotrichum* detected can include *Geotrichum candidum* or *Geotrichum klebahnii*.

In an alternative embodiment, the device detects spores from the plant pathogen *Galactomyces*. In one embodiment, the plant pathogen chemoattractant is a chemoattractant for one or more species of *Galactomyces*. In one embodiment, the at least one plant pathogen chemoattractant attracts multiple plant pathogens, including at least one species of *Galactomyces*. As used herein, the term "*Galactomyces*" includes all the species of the *Galactomyces*. The species of *Galactomyces* detected can include *Galactomyces geotrichum*.

In an alternative embodiment, the device detects spores from the plant pathogen *Sclerotinia*. In one embodiment, the plant pathogen chemoattractant is a chemoattractant for one or more species of *Sclerotinia*. In one embodiment, the at least one plant pathogen chemoattractant attracts multiple plant pathogens, including at least one species of *Sclerotinia*. As used herein, the term "*Sclerotinia*" includes all the species of the *Sclerotinia*. The species of *Sclerotinia* detected can include *Sclerotinia scierotiorum, Sclerotinia minor, Sclerotinia trifoliorum* or *Sclerotinia cinerea*.

In an alternative embodiment, the device detects spores from the plant pathogen *Sclerotium*. In one embodiment, the plant pathogen chemoattractant is a chemoattractant for one or more species of *Sclerotium*. In one embodiment, the at least one plant pathogen chemoattractant attracts multiple plant pathogens, including at least one species of *Sclerotium*. As used herein, the term "*Sclerotium*" includes all the species of the *Sclerotium*. The species of *Sclerotium* detected can include *Sclerotium delphinii* and *Sclerotium rolfsii*.

In an alternative embodiment, the device detects spores from the plant pathogen *Athelia*. In one embodiment, the plant pathogen chemoattractant is a chemoattractant for one or more species of *Athelia*. In one embodiment, the at least one plant pathogen chemoattractant attracts multiple plant pathogens, including at least one species of *Athelia*. As used herein, the term "*Athelia*" includes all the species of the *Athelia*. The species of *Athelia* detected can include *Athelia rolfsii*.

In an alternative embodiment, the device detects spores from the plant pathogen *Corynespora*. In one embodiment, the plant pathogen chemoattractant is a chemoattractant for one or more species of *Corynespora*. In one embodiment, the at least one plant pathogen chemoattractant attracts multiple plant pathogens, including at least one species of *Corynespora*. As used herein, the term "*Corynespora*" includes all the species of the *Corynespora*. The species of *Corynespora* detected can include *Corynespora cassiicola*.

In an alternative embodiment, the device detects spores from the plant pathogen *Verticillium*. In one embodiment, the plant pathogen chemoattractant is a chemoattractant for one or more species of *Verticillium*. In one embodiment, the at least one plant pathogen chemoattractant attracts multiple plant pathogens, including at least one species of *Verticillium*. As used herein, the term "*Verticillium*" includes all the species of the *Verticillium*. The species of *Verticillium* detected can include *Verticillium albo-atrum* or *Verticillium dahlia*.

In an alternative embodiment, the device detects spores from the plant pathogen *Acremonium*. In one embodiment, the plant pathogen chemoattractant is a chemoattractant for one or more species of *Acremonium*. In one embodiment, the at least one plant pathogen chemoattractant attracts multiple plant pathogens, including at least one species of *Acremonium*. As used herein, the term "*Acremonium*" includes all the species of the *Acremonium*. The species of *Acremonium* detected can include *Acremonium strictum*.

In an alternative embodiment, the device detects spores from the plant pathogen *Cephalosporium*. In one embodiment, the plant pathogen chemoattractant is a chemoattractant for one or more species of *Cephalosporium*. In one embodiment, the at least one plant pathogen chemoattractant attracts multiple plant pathogens, including at least one species of *Cephalosporium*. As used herein, the term "*Cephalosporium*" includes all the species of the *Cephalosporium*. The species of *Cephalosporium* detected can include *Cephalosporium maydis* or *Cephalosporium acremonium*.

In an alternative embodiment, the device detects spores from the plant pathogen *Lasiodiplodia*. In one embodiment, the plant pathogen chemoattractant is a chemoattractant for one or more species of *Lasiodiplodia*. In one embodiment, the at least one plant pathogen chemoattractant attracts multiple plant pathogens, including at least one species of *Lasiodiplodia*. As used herein, the term "*Lasiodiplodia*" includes all the species of the *Lasiodiplodia*. The species of *Lasiodiplodia* detected can include *Lasiodiplodia theobromae*.

In an alternative embodiment, the device detects spores from the plant pathogen *Botryodiplodia*. In one embodiment, the plant pathogen chemoattractant is a chemoattractant for one or more species of *Botryodiplodia*. In one embodiment, the at least one plant pathogen chemoattractant attracts multiple plant pathogens, including at least one species of *Botryodiplodia*. As used herein, the term "*Botryodiplodia*" includes all the species of the *Botryodiplodia*. The species of *Botryodiplodia* detected can include *Botryodiplodia theobromae*.

In an alternative embodiment, the device detects spores from the plant pathogen *Physoderma*. In one embodiment, the plant pathogen chemoattractant is a chemoattractant for one or more species of *Physoderma*. In one embodiment, the at least one plant pathogen chemoattractant attracts multiple plant pathogens, including at least one species of *Physoderma*. As used herein, the term "*Physoderma*" includes all the species of the *Physoderma*. The species of *Physoderma* detected can include *Physoderma maydis*.

In an alternative embodiment, the device detects spores from the plant pathogen *Physalospora*. In one embodiment, the plant pathogen chemoattractant is a chemoattractant for one or more species of *Physalospora*. In one embodiment, the at least one plant pathogen chemoattractant attracts multiple plant pathogens, including at least one species of *Physalospora*. As used herein, the term "*Physalospora*" includes all the species of the *Physalospora*. The species of *Physalospora* detected can include *Physalospora zeicola* or *Physalospora zeae*.

In an alternative embodiment, the device detects spores from the plant pathogen *Diplodia*. In one embodiment, the plant pathogen chemoattractant is a chemoattractant for one or more species of *Diplodia*. In one embodiment, the at least one plant pathogen chemoattractant attracts multiple plant pathogens, including at least one species of *Diplodia*. As used herein, the term "*Diplodia*" includes all the species of the *Diplodia*. The species of *Diplodia* detected can include any of *Diplodia zeae, Diplodia frumenti, Diplodia maydis* or *Diplodia macrospora*.

In an alternative embodiment, the device detects spores from the plant pathogen *Botryosphaeria*. In one embodiment, the plant pathogen chemoattractant is a chemoattractant for one or more species of *Botryosphaeria*. In one embodiment, the at least one plant pathogen chemoattractant attracts multiple plant pathogens, including at least one species of *Botryosphaeria*. As used herein, the term "*Botry-*

*osphaeria*" includes all the species of the *Botryosphaeria*. The species of *Botryosphaeria* detected can include *Botryosphaeria zeae* or *Botryosphaeria festucae*.

In an alternative embodiment, the device detects spores from the plant pathogen *Stenocarpella*. In one embodiment, the plant pathogen chemoattractant is a chemoattractant for one or more species of *Stenocarpella*. In one embodiment, the at least one plant pathogen chemoattractant attracts multiple plant pathogens, including at least one species of *Stenocarpella*. As used herein, the term "*Stenocarpella*" includes all the species of the *Stenocarpella*. The species of *Stenocarpella* detected can include *Stenocarpella maydis* or *Stenocarpella macrocspora*.

In an alternative embodiment, the device detects spores from the plant pathogen *Sclerophthora*. In one embodiment, the plant pathogen chemoattractant is a chemoattractant for one or more species of *Sclerophthora*. In one embodiment, the at least one plant pathogen chemoattractant attracts multiple plant pathogens, including at least one species of *Sclerophthora*. As used herein, the term "*Sclerophthora*" includes all the species of the *Sclerophthora*. The species of *Sclerophthora* detected can include *Sclerophthora rayssiae* or *Sclerophthora macrospora*.

In an alternative embodiment, the device detects spores from the plant pathogen *Sclerospora*. In one embodiment, the plant pathogen chemoattractant is a chemoattractant for one or more species of *Sclerospora*. In one embodiment, the at least one plant pathogen chemoattractant attracts multiple plant pathogens, including at least one species of *Sclerospora*. As used herein, the term "*Sclerospora*" includes all the species of the *Sclerospora*. The species of *Sclerospora* detected can include any of *Sclerospora maydis*, *Sclerospora graminicola*, *Sclerospora philippinensis*, *Sclerospora sorghi*, *Sclerospora spontanea* or *Sclerospora sacchari*.

In an alternative embodiment, the device detects spores from the plant pathogen *Peronosclerospora*. In one embodiment, the plant pathogen chemoattractant is a chemoattractant for one or more species of *Peronosclerospora*. In one embodiment, the at least one plant pathogen chemoattractant attracts multiple plant pathogens, including at least one species of *Peronosclerospora*. As used herein, the term "*Peronosclerospora*" includes all the species of the *Peronosclerospora*. The species of *Peronosclerospora* detected can include any of *Peronosclerospora maydis*, *Peronosclerospora philippinensis*, *Peronosclerospora sorghi*, *Peronosclerospora spontanea* or *Peronosclerospora sacchari*.

In an alternative embodiment, the device detects spores from the plant pathogen *Nigrospora*. In one embodiment, the plant pathogen chemoattractant is a chemoattractant for one or more species of *Nigrospora*. In one embodiment, the at least one plant pathogen chemoattractant attracts multiple plant pathogens, including at least one species of *Nigrospora*. As used herein, the term "*Nigrospora*" includes all the species of the *Nigrospora*. The species of *Nigrospora* detected can include *Nigrospora oryzae*.

In an alternative embodiment, the device detects spores from the plant pathogen *Khuskia*. In one embodiment, the plant pathogen chemoattractant is a chemoattractant for one or more species of *Khuskia*. In one embodiment, the at least one plant pathogen chemoattractant attracts multiple plant pathogens, including at least one species of *Khuskia*. As used herein, the term "*Khuskia*" includes all the species of the *Khuskia*. The species of *Khuskia* detected can include *Khuskia oryzae*.

In an alternative embodiment, the device detects spores from the plant pathogen *Trichoderma*. In one embodiment, the plant pathogen chemoattractant is a chemoattractant for one or more species of *Trichoderma*. In one embodiment, the at least one plant pathogen chemoattractant attracts multiple plant pathogens, including at least one species of *Trichoderma*. As used herein, the term "*Trichoderma*" includes all the species of the *Trichoderma*. The species of *Trichoderma* detected can include *Trichoderma viride* or *Trichoderma lignorum*.

In an alternative embodiment, the device detects spores from the plant pathogen *Hypocrea*. In one embodiment, the plant pathogen chemoattractant is a chemoattractant for one or more species of *Hypocrea*. In one embodiment, the at least one plant pathogen chemoattractant attracts multiple plant pathogens, including at least one species of *Hypocrea*. As used herein, the term "*Hypocrea*" includes all the species of the *Hypocrea*.

In an alternative embodiment, the device detects spores from the plant pathogen *Phyllachora*. In one embodiment, the plant pathogen chemoattractant is a chemoattractant for one or more species of *Phyllachora*. In one embodiment, the at least one plant pathogen chemoattractant attracts multiple plant pathogens, including at least one species of *Phyllachora*. As used herein, the term "*Phyllachora*" includes all the species of the *Phyllachora*. The species of *Phyllachora* detected can include *Phyllachora maydis*.

In an alternative embodiment, the device detects spores from the plant pathogen *Botryotinia*. In one embodiment, the plant pathogen chemoattractant is a chemoattractant for one or more species of *Botryotinia*. In one embodiment, the at least one plant pathogen chemoattractant attracts multiple plant pathogens, including at least one species of *Botryotinia*. As used herein, the term "*Botryotinia*" includes all the species of the *Botryotinia*. The species of *Botryotinia* detected can include *Botryotinia fuckeliana*.

In an alternative embodiment, the device detects spores from the plant pathogen *Cunninghamella*. In one embodiment, the plant pathogen chemoattractant is a chemoattractant for one or more species of *Cunninghamella*. In one embodiment, the at least one plant pathogen chemoattractant attracts multiple plant pathogens, including at least one species of *Cunninghamella*. As used herein, the term "*Cunninghamella*" includes all the species of the *Cunninghamella*.

In an alternative embodiment, the device detects spores from the plant pathogen *Doratomyces*. In one embodiment, the plant pathogen chemoattractant is a chemoattractant for one or more species of *Doratomyces*. In one embodiment, the at least one plant pathogen chemoattractant attracts multiple plant pathogens, including at least one species of *Doratomyces*. As used herein, the term "*Doratomyces*" includes all the species of the *Doratomyces*. The species of *Doratomyces* detected can include *Doratomyces stemonitis*.

In an alternative embodiment, the device detects spores from the plant pathogen *Cephalotrichum*. In one embodiment, the plant pathogen chemoattractant is a chemoattractant for one or more species of *Cephalotrichum*. In one embodiment, the at least one plant pathogen chemoattractant attracts multiple plant pathogens, including at least one species of *Cephalotrichum*. As used herein, the term "*Cephalotrichum*" includes all the species of the *Cephalotrichum*. The species of *Cephalotrichum* detected can include *Cephalotrichum stemonitis*.

In an alternative embodiment, the device detects spores from the plant pathogen *Gonatobotrys*. In one embodiment, the plant pathogen chemoattractant is a chemoattractant for one or more species of *Gonatobotrys*. In one embodiment, the at least one plant pathogen chemoattractant attracts multiple plant pathogens, including at least one species of

*Gonatobotrys*. As used herein, the term "*Gonatobotrys*" includes all the species of the *Gonatobotrys*. The species of *Gonatobotrys* detected can include *Gonatobotrys simplex*.

In an alternative embodiment, the device detects spores from the plant pathogen *Pithomyces*. In one embodiment, the plant pathogen chemoattractant is a chemoattractant for one or more species of *Pithomyces*. In one embodiment, the at least one plant pathogen chemoattractant attracts multiple plant pathogens, including at least one species of *Pithomyces*. As used herein, the term "*Pithomyces*" includes all the species of the *Pithomyces*. The species of *Pithomyces* detected can include *Pithomyces maydicus*.

In an alternative embodiment, the device detects spores from the plant pathogen *Scopulariopsis*. In one embodiment, the plant pathogen chemoattractant is a chemoattractant for one or more species of *Scopulariopsis*. In one embodiment, the at least one plant pathogen chemoattractant attracts multiple plant pathogens, including at least one species of *Scopulariopsis*. As used herein, the term "*Scopulariopsis*" includes all the species of the *Scopulariopsis*. The species of *Scopulariopsis* detected can include *Scopulariopsis brumptii*.

In an alternative embodiment, the device detects spores from the plant pathogen *Claviceps*. In one embodiment, the plant pathogen chemoattractant is a chemoattractant for one or more species of *Claviceps*. In one embodiment, the at least one plant pathogen chemoattractant attracts multiple plant pathogens, including at least one species of *Claviceps*. As used herein, the term "*Claviceps*" includes all the species of the *Claviceps*. The species of *Claviceps* detected can include *Claviceps gigantean*.

In an alternative embodiment, the device detects spores from the plant pathogen *Sphacelia*. In one embodiment, the plant pathogen chemoattractant is a chemoattractant for one or more species of *Sphacelia*. In one embodiment, the at least one plant pathogen chemoattractant attracts multiple plant pathogens, including at least one species of *Sphacelia*. As used herein, the term "*Sphacelia*" includes all the species of the *Sphacelia*.

In an alternative embodiment, the device detects spores from the plant pathogen *Phyllosticta*. In one embodiment, the plant pathogen chemoattractant is a chemoattractant for one or more species of *Phyllosticta*. In one embodiment, the at least one plant pathogen chemoattractant attracts multiple plant pathogens, including at least one species of *Phyllosticta*. As used herein, the term "*Phyllosticta*" includes all the species of the *Phyllosticta*. The species of *Phyllosticta* detected can include *Phyllosticta maydis*.

In an alternative embodiment, the device detects spores from the plant pathogen *Mycosphaerella*. In one embodiment, the plant pathogen chemoattractant is a chemoattractant for one or more species of *Mycosphaerella*. In one embodiment, the at least one plant pathogen chemoattractant attracts multiple plant pathogens, including at least one species of *Mycosphaerella*. As used herein, the term "*Mycosphaerella*" includes all the species of the *Mycosphaerella*. The species of *Mycosphaerella* detected can include *Mycosphaerella zeae-maydis*.

In an alternative embodiment, the device detects spores from the plant pathogen *Gloeocercospora*. In one embodiment, the plant pathogen chemoattractant is a chemoattractant for one or more species of *Gloeocercospora*. In one embodiment, the at least one plant pathogen chemoattractant attracts multiple plant pathogens, including at least one species of *Gloeocercospora*. As used herein, the term "*Gloeocercospora*" includes all the species of the *Gloeocercospora*. The species of *Gloeocercospora* detected can include *Gloeocercospora sorghi*.

In an alternative embodiment, the device detects spores from the plant pathogen *Aureobasidium*. In one embodiment, the plant pathogen chemoattractant is a chemoattractant for one or more species of *Aureobasidium*. In one embodiment, the at least one plant pathogen chemoattractant attracts multiple plant pathogens, including at least one species of *Aureobasidium*. As used herein, the term "*Aureobasidium*" includes all the species of the *Aureobasidium*. The species of *Aureobasidium* detected can include *Aureobasidium zeae*.

In an alternative embodiment, the device detects spores from the plant pathogen *Kabatiella*. In one embodiment, the plant pathogen chemoattractant is a chemoattractant for one or more species of *Kabatiella*. In one embodiment, the at least one plant pathogen chemoattractant attracts multiple plant pathogens, including at least one species of *Kabatiella*. As used herein, the term "*Kabatiella*" includes all the species of the *Kabatiella*. The species of *Kabatiella* detected can include *Kabatiella zeae*.

In an alternative embodiment, the device detects spores from the plant pathogen *Exserohilum*. In one embodiment, the plant pathogen chemoattractant is a chemoattractant for one or more species of *Exserohilum*. In one embodiment, the at least one plant pathogen chemoattractant attracts multiple plant pathogens, including at least one species of *Exserohilum*. As used herein, the term "*Exserohilum*" includes all the species of the *Exserohilum*. The species of *Exserohilum* detected can include any of *Exserohilum turcicum, Exserohilum prolatum* or *Exserohilum pedicellatum*.

In an alternative embodiment, the device detects spores from the plant pathogen *Helminthosporium*. In one embodiment, the plant pathogen chemoattractant is a chemoattractant for one or more species of *Helminthosporium*. In one embodiment, the at least one plant pathogen chemoattractant attracts multiple plant pathogens, including at least one species of *Helminthosporium*. As used herein, the term "*Helminthosporium*" includes all the species of the *Helminthosporium*. The species of *Helminthosporium* detected can include any of *Helminthosporium rostratum, Helminthosporium carbonum, Helminthosporium turcicum, Helminthosporium sativum, Helminthosporium victoriae, Helminthosporium pedicellatum* or *Helminthosporium sorokinianum*.

In an alternative embodiment, the device detects spores from the plant pathogen *Setosphaeria*. In one embodiment, the plant pathogen chemoattractant is a chemoattractant for one or more species of *Setosphaeria*. In one embodiment, the at least one plant pathogen chemoattractant attracts multiple plant pathogens, including at least one species of *Setosphaeria*. As used herein, the term "*Setosphaeria*" includes all the species of the *Setosphaeria*. The species of *Setosphaeria* detected can include any of *Setosphaeria rostrate, Setosphaeria turcica, Setosphaeria prolata* or *Setosphaeria pedicellatum.*

In an alternative embodiment, the device detects spores from the plant pathogen *Hyalothyridium*. In one embodiment, the plant pathogen chemoattractant is a chemoattractant for one or more species of *Hyalothyridium*. In one embodiment, the at least one plant pathogen chemoattractant attracts multiple plant pathogens, including at least one species of *Hyalothyridium*. As used herein, the term "*Hyalothyridium*" includes all the species of the *Hyalothyridium*. The species of *Hyalothyridium* detected can include *Hyalothyridium maydis.*

In an alternative embodiment, the device detects spores from the plant pathogen *Ascochyta*. In one embodiment, the plant pathogen chemoattractant is a chemoattractant for one or more species of *Ascochyta*. In one embodiment, the at least one plant pathogen chemoattractant attracts multiple plant pathogens, including at least one species of *Ascochyta*. As used herein, the term "*Ascochyta*" includes all the species of the *Ascochyta*. The species of *Ascochyta* detected can include *Ascochyta maydi, Ascochyta tritici, Ascochyta zeicola* or *Ascochyta ischaemi*.

In an alternative embodiment, the device detects spores from the plant pathogen *Bipolaris*. In one embodiment, the plant pathogen chemoattractant is a chemoattractant for one or more species of *Bipolaris*. In one embodiment, the at least one plant pathogen chemoattractant attracts multiple plant pathogens, including at least one species of *Bipolaris*. As used herein, the term "*Bipolaris*" includes all the species of the *Bipolaris*. The species of *Bipolaris* detected can include *Bipolaris sorokiniana, Bipolaris zeicola, Bipolaris victoriae* or *Bipolaris sorokiniana*.

In an alternative embodiment, the device detects spores from the plant pathogen *Epicoccum*. In one embodiment, the plant pathogen chemoattractant is a chemoattractant for one or more species of *Epicoccum*. In one embodiment, the at least one plant pathogen chemoattractant attracts multiple plant pathogens, including at least one species of *Epicoccum*. As used herein, the term "*Epicoccum*" includes all the species of the *Epicoccum*. The species of *Epicoccum* detected can include *Epicoccum nigrum*.

In an alternative embodiment, the device detects spores from the plant pathogen *Drechslera*. In one embodiment, the plant pathogen chemoattractant is a chemoattractant for one or more species of *Drechslera*. In one embodiment, the at least one plant pathogen chemoattractant attracts multiple plant pathogens, including at least one species of *Drechslera*. As used herein, the term "*Drechslera*" includes all the species of the *Drechslera*. The species of *Drechslera* detected can include *Drechslera prolata*.

In an alternative embodiment, the device detects spores from the plant pathogen *Graphium*. In one embodiment, the plant pathogen chemoattractant is a chemoattractant for one or more species of *Graphium*. In one embodiment, the at least one plant pathogen chemoattractant attracts multiple plant pathogens, including at least one species of *Graphium*. As used herein, the term "*Graphium*" includes all the species of the *Graphium*. The species of *Graphium* detected can include *Graphium penicilliodes*.

In an alternative embodiment, the device detects spores from the plant pathogen *Leptosphaeria*. In one embodiment, the plant pathogen chemoattractant is a chemoattractant for one or more species of *Leptosphaeria*. In one embodiment, the at least one plant pathogen chemoattractant attracts multiple plant pathogens, including at least one species of *Leptosphaeria*. As used herein, the term "*Leptosphaeria*" includes all the species of the *Leptosphaeria*. The species of *Leptosphaeria* detected can include *Leptosphaeria maydis* or *Leptosphaeria zeae*.

In an alternative embodiment, the device detects spores from the plant pathogen *Ophiosphaerella*. In one embodiment, the plant pathogen chemoattractant is a chemoattractant for one or more species of *Ophiosphaerella*. In one embodiment, the at least one plant pathogen chemoattractant attracts multiple plant pathogens, including at least one species of *Ophiosphaerella*. As used herein, the term "*Ophiosphaerella*" includes all the species of the *Ophiosphaerella*. The species of *Ophiosphaerella* detected can include *Ophiosphaerella herpotricha*.

In an alternative embodiment, the device detects spores from the plant pathogen *Scolecosporiella*. In one embodiment, the plant pathogen chemoattractant is a chemoattractant for one or more species of *Scolecosporiella*. In one embodiment, the at least one plant pathogen chemoattractant attracts multiple plant pathogens, including at least one species of *Scolecosporiella*. As used herein, the term "*Scolecosporiella*" includes all the species of the *Scolecosporiella*.

In an alternative embodiment, the device detects spores from the plant pathogen *Paraphaeosphaeria*. In one embodiment, the plant pathogen chemoattractant is a chemoattractant for one or more species of *Paraphaeosphaeria*. In one embodiment, the at least one plant pathogen chemoattractant attracts multiple plant pathogens, including at least one species of *Paraphaeosphaeria*. As used herein, the term "*Paraphaeosphaeria*" includes all the species of the *Paraphaeosphaeria*. The species of *Paraphaeosphaeria* detected can include *Paraphaeosphaeria michotii*.

In an alternative embodiment, the device detects spores from the plant pathogen *Phoma*. In one embodiment, the plant pathogen chemoattractant is a chemoattractant for one or more species of *Phoma*. In one embodiment, the at least one plant pathogen chemoattractant attracts multiple plant pathogens, including at least one species of *Phoma*. As used herein, the term "*Phoma*" includes all the species of the *Phoma*.

In an alternative embodiment, the device detects spores from the plant pathogen *Septoria*. In one embodiment, the plant pathogen chemoattractant is a chemoattractant for one or more species of *Septoria*. In one embodiment, the at least one plant pathogen chemoattractant attracts multiple plant pathogens, including at least one species of *Septoria*. As used herein, the term "*Septoria*" includes all the species of the *Septoria*. The species of *Septoria* detected can include any of *Septoria zeae, Septoria zeicola* or *Septoria zeina*.

In an alternative embodiment, the device detects spores from the plant pathogen *Penicillium*. In one embodiment, the plant pathogen chemoattractant is a chemoattractant for one or more species of *Penicillium*. In one embodiment, the at least one plant pathogen chemoattractant attracts multiple plant pathogens, including at least one species of *Penicillium*. As used herein, the term "*Penicillium*" includes all the species of the *Penicillium*. The species of *Penicillium* detected can include *Penicillium chrysogenum, Penicillium expansum* or *Penicillium oxalicum*.

In an alternative embodiment, the device detects spores from the plant pathogen *Phaeocytostroma*. In one embodiment, the plant pathogen chemoattractant is a chemoattractant for one or more species of *Phaeocytostroma*. In one embodiment, the at least one plant pathogen chemoattractant attracts multiple plant pathogens, including at least one species of *Phaeocytostroma*. As used herein, the term "*Phaeocytostroma*" includes all the species of the *Phaeocytostroma*. The species of *Phaeocytostroma* detected can include *Phaeocytostroma ambiguum, Phaeocytostroma zaea* or *Phaeocytostroma maydis*.

In an alternative embodiment, the device detects spores from the plant pathogen *Sphaerulina*. In one embodiment, the plant pathogen chemoattractant is a chemoattractant for one or more species of *Sphaerulina*. In one embodiment, the at least one plant pathogen chemoattractant attracts multiple plant pathogens, including at least one species of *Sphaerulina*. As used herein, the term "*Sphaerulina*" includes all the species of the *Sphaerulina*. The species of *Sphaerulina* detected can include *Sphaerulina maydis*.

In an alternative embodiment, the device detects spores from the plant pathogen *Dictochaeta*. In one embodiment, the plant pathogen chemoattractant is a chemoattractant for one or more species of *Dictochaeta*. In one embodiment, the at least one plant pathogen chemoattractant attracts multiple plant pathogens, including at least one species of *Dictochaeta*. As used herein, the term "*Dictochaeta*" includes all the species of the *Dictochaeta*. The species of *Dictochaeta* detected can include *Dictochaeta fertilis*.

In an alternative embodiment, the device detects spores from the plant pathogen *Microdochium*. In one embodiment, the plant pathogen chemoattractant is a chemoattractant for one or more species of *Microdochium*. In one embodiment, the at least one plant pathogen chemoattractant attracts multiple plant pathogens, including at least one species of *Microdochium*. As used herein, the term "*Microdochium*" includes all the species of the *Microdochium*. The species of *Microdochium* detected can include *Microdochium bolleyi*.

In an alternative embodiment, the device detects spores from the plant pathogen *Mucor*. In one embodiment, the plant pathogen chemoattractant is a chemoattractant for one or more species of *Mucor*. In one embodiment, the at least one plant pathogen chemoattractant attracts multiple plant pathogens, including at least one species of *Mucor*. As used herein, the term "*Mucor*" includes all the species of the *Mucor*.

In an alternative embodiment, the device detects spores from the plant pathogen *Mariannaea*. In one embodiment, the plant pathogen chemoattractant is a chemoattractant for one or more species of *Mariannaea*. In one embodiment, the at least one plant pathogen chemoattractant attracts multiple plant pathogens, including at least one species of *Mariannaea*. As used herein, the term "*Mariannaea*" includes all the species of the *Mariannaea*. The species of *Mariannaea* detected can include *Mariannaea elegans*.

In an alternative embodiment, the device detects spores from the plant pathogen *Periconia*. In one embodiment, the plant pathogen chemoattractant is a chemoattractant for one or more species of *Periconia*. In one embodiment, the at least one plant pathogen chemoattractant attracts multiple plant pathogens, including at least one species of *Periconia*. As used herein, the term "*Periconia*" includes all the species of the *Periconia*. The species of *Periconia* detected can include *Periconia circinata*.

In an alternative embodiment, the device detects spores from the plant pathogen *Physopella*. In one embodiment, the plant pathogen chemoattractant is a chemoattractant for one or more species of *Physopella*. In one embodiment, the at least one plant pathogen chemoattractant attracts multiple plant pathogens, including at least one species of *Physopella*. As used herein, the term "*Physopella*" includes all the species of the *Physopella*. The species of *Physopella* detected can include *Physopella pallescens* or *Physopella zeae*.

In an alternative embodiment, the device detects spores from the plant pathogen *Rhopographus*. In one embodiment, the plant pathogen chemoattractant is a chemoattractant for one or more species of *Rhopographus*. In one embodiment, the at least one plant pathogen chemoattractant attracts multiple plant pathogens, including at least one species of *Rhopographus*. As used herein, the term "*Rhopographus*" includes all the species of the *Rhopographus*. The species of *Rhopographus* detected can include *Rhopographus zeae*.

In an alternative embodiment, the device detects spores from the plant pathogen *Spicaria*. In one embodiment, the plant pathogen chemoattractant is a chemoattractant for one or more species of *Spicaria*. In one embodiment, the at least one plant pathogen chemoattractant attracts multiple plant pathogens, including at least one species of *Spicaria*. As used herein, the term "*Spicaria*" includes all the species of the *Spicaria*.

In an alternative embodiment, the device detects spores from the plant pathogen *Angiopsora*. In one embodiment, the plant pathogen chemoattractant is a chemoattractant for one or more species of *Angiopsora*. In one embodiment, the at least one plant pathogen chemoattractant attracts multiple plant pathogens, including at least one species of *Angiopsora*. As used herein, the term "*Angiopsora*" includes all the species of the *Angiopsora*. The species of *Angiopsora* detected can include *Angiopsora zeae*.

In an alternative embodiment, the device detects spores from the plant pathogen *Nectria*. In one embodiment, the plant pathogen chemoattractant is a chemoattractant for one or more species of *Nectria*. In one embodiment, the at least one plant pathogen chemoattractant attracts multiple plant pathogens, including at least one species of *Nectria*. As used herein, the term "*Nectria*" includes all the species of the *Nectria*. The species of *Nectria* detected can include *Nectria haematococca*.

In an alternative embodiment, the device detects spores from the plant pathogen *Phomopsis*. In one embodiment, the plant pathogen chemoattractant is a chemoattractant for one or more species of *Phomopsis*. In one embodiment, the at least one plant pathogen chemoattractant attracts multiple plant pathogens, including at least one species of *Phomopsis*. As used herein, the term "*Phomopsis*" includes all the species of the *Phomopsis*.

In an alternative embodiment, the device detects spores from the plant pathogen *Spicaria*. In one embodiment, the plant pathogen chemoattractant is a chemoattractant for one or more species of *Spicaria*. In one embodiment, the at least one plant pathogen chemoattractant attracts multiple plant pathogens, including at least one species of *Spicaria*. As used herein, the term "*Spicaria*" includes all the species of the *Spicaria*.

In an alternative embodiment, the device detects spores from the plant pathogen *Selenophoma*. In one embodiment, the plant pathogen chemoattractant is a chemoattractant for one or more species of *Selenophoma*. In one embodiment, the at least one plant pathogen chemoattractant attracts multiple plant pathogens, including at least one species of *Selenophoma*. As used herein, the term "*Selenophoma*" includes all the species of the *Selenophoma*.

In an alternative embodiment, the device detects spores from the plant pathogen *Gaeumannomyces*. In one embodiment, the plant pathogen chemoattractant is a chemoattractant for one or more species of *Gaeumannomyces*. In one embodiment, the at least one plant pathogen chemoattractant attracts multiple plant pathogens, including at least one species of *Gaeumannomyces*. As used herein, the term "*Gaeumannomyces*" includes all the species of the *Gaeumannomyces*. The species of *Gaeumannomyces* detected can include *Gaeumannomyces graminis*.

In an alternative embodiment, the device detects spores from the plant pathogen *Myrothecium*. In one embodiment, the plant pathogen chemoattractant is a chemoattractant for one or more species of *Myrothecium*. In one embodiment, the at least one plant pathogen chemoattractant attracts multiple plant pathogens, including at least one species of *Myrothecium*. As used herein, the term "*Myrothecium*" includes all the species of the *Myrothecium*. The species of *Myrothecium* detected can include *Myrothecium gramineum*.

In an alternative embodiment, the device detects spores from the plant pathogen *Monascus*. In one embodiment, the plant pathogen chemoattractant is a chemoattractant for one or more species of *Monascus*. In one embodiment, the at least one plant pathogen chemoattractant attracts multiple plant pathogens, including at least one species of *Monascus*. As used herein, the term "*Monascus*" includes all the species of the *Monascus*. The species of *Monascus* detected can include *Monascus purpureus*.

In an alternative embodiment, the device detects spores from the plant pathogen *Bremiella*. In one embodiment, the plant pathogen chemoattractant is a chemoattractant for one or more species of *Bremiella*. In one embodiment, the at least one plant pathogen chemoattractant attracts multiple plant pathogens, including at least one species of *Bremiella*. As used herein, the term "*Bremiella*" includes all the species of the *Bremiella*.

In an alternative embodiment, the device detects spores from the plant pathogen *Pseudoperonospora*. In one embodiment, the plant pathogen chemoattractant is a chemoattractant for one or more species of *Pseudoperonospora*. In one embodiment, the at least one plant pathogen chemoattractant attracts multiple plant pathogens, including at least one species of *Pseudoperonospora*. As used herein, the term "*Pseudoperonospora*" includes all the species of the *Pseudoperonospora*.

In an alternative embodiment, the device detects spores from the plant pathogen *Rhizophydium*. In one embodiment, the plant pathogen chemoattractant is a chemoattractant for one or more species of *Rhizophydium*. In one embodiment, the at least one plant pathogen chemoattractant attracts multiple plant pathogens, including at least one species of *Rhizophydium*. As used herein, the term "*Rhizophydium*" includes all the species of the *Rhizophydium*.

In an alternative embodiment, the device detects spores from the plant pathogen *Synchytrium*. In one embodiment, the plant pathogen chemoattractant is a chemoattractant for one or more species of *Synchytrium*. In one embodiment, the at least one plant pathogen chemoattractant attracts multiple plant pathogens, including at least one species of *Synchytrium*. As used herein, the term "*Synchytrium*" includes all the species of the *Synchytrium*.

In an alternative embodiment, the device detects spores from the plant pathogen *Olpidium*. In one embodiment, the plant pathogen chemoattractant is a chemoattractant for one or more species of *Olpidium*. In one embodiment, the at least one plant pathogen chemoattractant attracts multiple plant pathogens, including at least one species of *Olpidium*. As used herein, the term "*Olpidium*" includes all the species of the *Olpidium*.

In an alternative embodiment, the device detects spores from the plant pathogen *Ligniera*. In one embodiment, the plant pathogen chemoattractant is a chemoattractant for one or more species of *Ligniera*. In one embodiment, the at least one plant pathogen chemoattractant attracts multiple plant pathogens, including at least one species of *Ligniera*. As used herein, the term "*Ligniera*" includes all the species of the *Ligniera*.

In an alternative embodiment, the device detects spores from the plant pathogen *Plasmidiophora*. In one embodiment, the plant pathogen chemoattractant is a chemoattractant for one or more species of *Plasmidiophora*. In one embodiment, the at least one plant pathogen chemoattractant attracts multiple plant pathogens, including at least one species of *Plasmidiophora*. As used herein, the term "*Plasmidiophora*" includes all the species of the *Plasmidiophora*.

In an alternative embodiment, the device detects spores from the plant pathogen *Polymixia*. In one embodiment, the plant pathogen chemoattractant is a chemoattractant for one or more species of *Polymixia*. In one embodiment, the at least one plant pathogen chemoattractant attracts multiple plant pathogens, including at least one species of *Polymixia*. As used herein, the term "*Polymixia*" includes all the species of the *Polymixia*.

In an alternative embodiment, the device detects spores from the plant pathogen *Sorodiscus*. In one embodiment, the plant pathogen chemoattractant is a chemoattractant for one or more species of *Sorodiscus*. In one embodiment, the at least one plant pathogen chemoattractant attracts multiple plant pathogens, including at least one species of *Sorodiscus*. As used herein, the term "*Sorodiscus*" includes all the species of the *Sorodiscus*.

In an alternative embodiment, the device detects spores from the plant pathogen *Sorosphaera*. In one embodiment, the plant pathogen chemoattractant is a chemoattractant for one or more species of *Sorosphaera*. In one embodiment, the at least one plant pathogen chemoattractant attracts multiple plant pathogens, including at least one species of *Sorosphaera*. As used herein, the term "*Sorosphaera*" includes all the species of the *Sorosphaera*.

In an alternative embodiment, the device detects spores from the plant pathogen *Spongospora*. In one embodiment, the plant pathogen chemoattractant is a chemoattractant for one or more species of *Spongospora*. In one embodiment, the at least one plant pathogen chemoattractant attracts multiple plant pathogens, including at least one species of *Spongospora*. As used herein, the term "*Spongospora*" includes all the species of the *Spongospora*.

In an alternative embodiment, the device detects spores from the plant pathogen *Tetramyxa*. In one embodiment, the plant pathogen chemoattractant is a chemoattractant for one or more species of *Tetramyxa*. In one embodiment, the at least one plant pathogen chemoattractant attracts multiple plant pathogens, including at least one species of *Tetramyxa*. As used herein, the term "*Tetramyxa*" includes all the species of the *Tetramyxa*.

In an alternative embodiment, the device detects spores from the plant pathogen *Aspergillus*. In one embodiment, the plant pathogen chemoattractant is a chemoattractant for one or more species of *Aspergillus*. In one embodiment, the at least one plant pathogen chemoattractant attracts multiple plant pathogens, including at least one species of *Aspergillus*. As used herein, the term "*Aspergillus*" includes all the species of the *Aspergillus*. The species of *Aspergillus* detected can include any of *Aspergillus glaucus, Aspergillus tubingensis, Aspergillus niger, Aspergillus flavus, Aspergillus candidus, Aspergillus columnaris, Aspergillus flavipes, Aspergillus fumigatus, Aspergillus ochraceus* or *Aspergillus tamarii*.

The device can detect one plant pathogen as detailed herein or alternatively may detect one or more plant pathogens as listed herein. The device may detect one, two, three, four, five, six, seven, eight, nine, ten or more plant pathogens.

The device of the invention comprises a support member (1) which contains at least one plant pathogen chemoattractant. The support member is typically of any suitable shape or size that allows it to support the remainder of the device, and typically allows the device to remain upright when placed in the soil or water surrounding a plant. The support member is typically the only part of the device that is in contact with the soil or water when in use. The support member typically remains stable when left in the soil or water for several days or weeks. The support member contains at least one plant pathogen chemoattractant, which serves to attract spores from a plant pathogen into the device, typically from soil or water. The support member therefore acts as bait for spores of a plant pathogen. The support member typically comprises any material capable of allowing the plant pathogen spore to flow from one end of the support member to the other by chemotaxis. The support member is typically made of a non-biodegradable material. In one embodiment, the support member is made of a non-porous material. In one embodiment, the support member includes a membrane. For example, the support member may be a solid support with a membrane coated on the solid support or dried on to the surface of the solid support. The membrane can be made from any suitable material, including but not limited to cellulose acetate membranes, mixed cellulose ester membranes, hydrophillic polytetrafluoroethylene membranes, hydrophobic polytetrafluoroethylene membranes, uncharged nylon membranes, charged nylon membranes, polycarbonate membranes, polyamide membranes, aluminium oxide membranes, polypropylene membranes, polyethersulfone membranes, nitrocellulose membrane, immunostick, polivinylidene difluoride membrane, positively charged nylon membranes or zeta-probe nylon membrane or filter paper. The membrane absorbs chemoattractant and a skilled person would be able to select an appropriate membrane. In one embodiment, the support member comprises more than one different membranes. In one embodiment, the support member comprises a plastic dipstick with a membrane of nitrocellulose or nylon attached thereto.

As described herein, the support member contains at least one plant pathogen chemoattractant that attracts a plant pathogen spore of interest. As used herein, the term "spore" includes any type of spore produced by fungi and fungal-like organisms, including motile spores such as zoospores. Detection of zoospores is a preferred embodiment of the present invention.

As used herein, the term "plant pathogen chemoattractant" includes any substance which attracts motile plant pathogen spores. The plant pathogen chemoattractant can be selected from amino acids (for example, aspartic acid, glutamic acid), alcohols (for example, ethanol, isopropanol or methanol), plant extract or specific plant compounds such as phytohormones, plant proteins, or plant signalling compounds, sugars, organic acids, phenolics or other proteins, such as casein, pectin and any derivatives of these.

The plant pathogen chemoattractant is typically specific for the plant pathogen spore to be detected. In one embodiment, the support member contains one, two, three, four, five, six, seven, eight, nine or ten different plant pathogen chemoattractants. The plant pathogen chemoattractants may be specific for one type of plant pathogen or alternatively the chemoattractant may attract more than one type of plant pathogen. In one embodiment, the plant pathogen chemoattractants are specific for two, three, four, five, six, seven, eight, nine or ten different plant pathogens. Alternatively, the different plant pathogen chemoattractants used may be specific for different plant pathogens i.e., the specicity of the chemoattractant may be chosen such that they do not overlap. The person skilled in the art will be able to select appropriate plant pathogen chemoattractants from commercially available chemoattractants. The person skilled in the art will be able to synthesize an appropriate plant pathogen chemoattractant using standard literature protocols. Typically, each plant pathogen chemoattractant used in the device is specific for the same plant pathogen. More typically, the same plant pathogen chemoattractant or combination thereof is used in each component of the device, as described herein.

In a preferred embodiment, the at least one plant pathogen chemoattractant is a chemoattractant for *Phytophthora*. Examples of chemoattractants for *Phytophthora cinnamomi* are described in Cahill and Hardman (*Phytopathology*, Vol. 84, No. 2, 1994, pages 193-200). In one embodiment, the at least one plant pathogen chemoattractant attracts one or more species of *Phytophthora*. In some embodiments, the at least one plant pathogen chemoattractant can attract more than one plant pathogen. In one embodiment, the at least one plant pathogen chemoattractant attracts one or more species of *Phytophthora* and one or more other plant pathogens. In one embodiment, the at least one plant pathogen chemoattractant is present on the support member in a concentration gradient. In one embodiment, the at least one plant pathogen chemoattractant is present at a higher concentration at the end of the support member adjacent to the filter than at the end of the support member not adjacent to the filter. In other words, the concentration of the at least one plant pathogen chemoattractant is lower at the end of the support member that will be in contact with the soil or water when in use (indicated as 1B in FIG. 1) than at the opposite end (indicated as 1A in FIG. 1). In one embodiment, the support member comprises two or more, three or more, four or more, five or more, six or more, seven or more, eight or more, nine or more, or ten or more different plant pathogen chemoattractants. In some embodiments, two or more, three or more, four or more, five or more, six or more, seven or more, eight or more, nine or more, or ten or more different plant pathogen chemoattractants are present on the support member in a concentration gradient.

The device of the invention comprises a filter (2) with a plurality of pores. The filter is used to selectively allow only the plant pathogen spore being detected to reach the culture medium (3). By using a selective filter in combination with chemoattractant(s) for a specific plant pathogen spore of interest the device can detect a plant pathogen of interest. In one embodiment, the filter comprises circular pores. In another embodiment, the filter comprises non-circular pores. In another embodiment, the filter comprises pores of irregular shape. In some embodiments, the filter can comprise pores of one shape and pores of a second shape. In one embodiment, the filter comprises pores of a first shape and an equal number of pores of a second shape. In one embodiment, the filter comprises a number of pores of a first shape and a lower number of pores of a second shape.

In one embodiment, the device comprises a first filter (2) comprising a plurality of pores, a second filter (4) comprising a plurality of pores and a second culture medium (5). The two filters are used to selectively allow only the plant pathogen spore being detected to reach the second culture medium (5). The first filter (2) and second filter (4) selectively allow spores of a specified size through the pores of each filter. By using selective filters in combination with chemoattractant(s) for a specific plant pathogen spore of interest the device can detect a plant pathogen of interest. In one embodiment, the first filter and/or second filter comprise circular pores. In another embodiment, the first filter and/or second filter comprise non-circular pores. In another embodiment, the first filter and/or second filter comprise pores of irregular shape. In some embodiments, the first filter and/or second filter can comprise pores of one shape and pores of a second shape. In one embodiment, the first filter and/or second filter comprise pores of a first shape and an equal number of pores of a second shape. In one embodiment, the first filter and/or second filter comprise a number of pores of a first shape and a lower number of pores of a second shape.

In one embodiment the first filter and second filter comprise an equal or almost equal number of pores. In one embodiment, the second filter comprises a lower number of pores than the first filter. In one embodiment, the first filter comprises a lower number of pores than the second filter.

The size of the pore determines the type of spore that will be able to pass through the pore, the pore size chosen reflecting the size of the spore of the plant pathogen to be detected. Spores larger than the spore of the plant pathogen to be detected will not be able to pass through the filter due to their larger size. Spores larger than the spore being detected, fungi and bacteria will therefore not pass through the pore of the filter.

In one embodiment, the first and/or second filter comprises pores with a size between about 5 and 150 µm, for example between about 5 and 10 µm, 10 and 15 µm, 15 and 20 µm, 20 and 25 µm, 25 and 30 µm, 30 and 35 µm, 35 and 40 µm, 40 and 45 µm, 45 and 50 µm, 50 and 55 µm, 55 and 60 µm, 60 and 65 µm, 65 and 70 µm, 70 and 75 µm, 75 and 80 µm, 80 and 85 µm, 85 and 90 µm, 90 and 95 µm, 95 and 100 µm, 100 and 105 µm, 105 and 110 µm, 110 and 115 µm, 115 and 120 µm, 120 and 125 µm, 125 and 130 µm, 130 and 135 µm, 135 and 140 µm, 140 and 145 µm or 145 and 150 µm.

In one embodiment, the size of the pores in the first filter is larger than the size of the pores in the second filter. In this embodiment, the different sizes of the pores of the first filter and second filter selectively allow only spores attracted to the at least one plant pathogen chemoattractant through the filter(s). In one embodiment, the first filter and/or the second filter comprises pores with a size between about 5 and 150 µm, for example between about 5 and 10 µm, 10 and 15 µm, 15 and 20 µm, 20 and 25 µm, 25 and 30 µm, 30 and 35 µm, 35 and 40 µm, 40 and 45 µm, 45 and 50 µm, 50 and 55 µm, 55 and 60 µm, 60 and 65 µm, 65 and 70 µm, 70 and 75 µm, 75 and 80 µm, 80 and 85 µm, 85 and 90 µm, 90 and 95 µm, 95 and 100 µm, 100 and 105 µm, 105 and 110 µm, 110 and 115 µm, 115 and 120 µm, 120 and 125 µm, 125 and 130 µm, 130 and 135 µm, 135 and 140 µm, 140 and 145 µm or 145 and 150 µm. In another embodiment, the first filter comprises pores with a size between about 80 and 120 µm and the second filter comprises pores with a size between about 50 and 70 µm. When the pores are circular or substantially circular, these sizes refer to the diameter of the pore.

In one embodiment, the size of the pores in the first filter is smaller than the size of the pores in the second filter. In this embodiment, the different sizes of the pores of the first and second filter selectively allow only spores attracted to the at least one plant pathogen chemoattractant through the filter(s). In one embodiment, the size of the pores in the first filter is equal or almost equal to the size of the pores in the second filter. The size of the pores of the first and/or second filter is selected dependent on the plant pathogen spore to be detected. This can be dependent on several factors, for example the growth rate of the plant pathogen spore of interest and the size of the plant pathogen spore in each of the culture media.

The filter can be of any suitable shape or size that allows the selective filtration of plant pathogen spores of interest. The filter can be of any suitable material that allows the selective filtration of a plant pathogen spore. The plant pathogen spores will pass through the filter by diffusion. In one embodiment the filter is made of a porous material. Examples of porous material include, but are not limited to nylon, nitrocellulose, a plastic, a ceramic, a fibre, matrigel or polymer. In one embodiment the filter is made of a non-porous material. In one embodiment, the filter is made of non-biodegradable material. A person skilled in the art would be able to contemplate suitable materials to form an appropriate filter. In one embodiment, the filter is a permeable membrane. The permeable membrane can be made of any suitable material that allows the selective filtration of a plant pathogen spore. In one embodiment, the filter can be made of cellulose acetate membranes, mixed cellulose ester membranes, hydrophillic polytetrafluoroethylene, hydrophobic polytetrafluoroethylene, charged nylon, uncharged nylon, polycarbonate, polyamide membranes, aluminium oxide membranes, polypropylene and polyethersulfone.

In some embodiments, the first filter and/or second filter can be of any suitable shape or size that allows the selective filtration of plant pathogen spores of interest. The first filter and/or second filter can be of any suitable material that allows the selective filtration of a plant pathogen spore. In one embodiment one or more of the filters is made of a porous material. Examples of porous material include, but are not limited to nylon, nitrocellulose, a plastic, a ceramic, a fibre, matrigel or polymer. In one embodiment one or more of the filters is made of a non-porous material. In one embodiment, one or more of the filters is made of non-biodegradable material. A person skilled in the art would be able to contemplate suitable materials to form an appropriate filter. In one embodiment, one or more of the filters is a permeable membrane. The permeable membrane can be made of any suitable material that allows the selective filtration of a plant pathogen spore. In one embodiment, the one or more filters can be made of cellulose acetate membranes, mixed cellulose ester membranes, hydrophillic polytetrafluoroethylene, hydrophobic polytetrafluoroethylene, charged nylon, uncharged nylon, polycarbonate, polyamide membranes, aluminium oxide membranes, polypropylene and polyethersulfone.

The device of the invention can contain other filters in addition to the first and optionally second filters. Accordingly, in some embodiments, the device comprises two, three, four, five, six, seven, eight, nine, ten or ten or more filters.

The device of the invention comprises a culture medium (3), which contains a at least one plant pathogen chemoattractant. The at least one plant pathogen chemoattractant will attract specific plant pathogens and they will travel through the filter to the culture medium by chemotaxis. In some embodiments, the culture medium can comprise additional plant pathogen chemoattractants, for example one, two, three, four, five, six, seven, eight, nine, ten, eleven, twelve, thirteen, fourteen, fifteen, sixteen, seventeen, eighteen, nineteen, twenty or twenty or more additional plant pathogen chemoattractants. The culture medium aids growth of the plant pathogen spore and can have many different compositions, depending on the pathogen spore being detected, which will be well understood by the person skilled in the art. In one embodiment, the culture medium is optimal for the survival of *Phytophthora*. Examples of suitable media are described in Jeffers and Martin (*Plant Disease*, 1986, Vol. 80 No. 11) and Guo and Ko (*Applied and Environmental Microbiology*, July 1993, Vol. 59, No. 7, p 2323-2325).

In one embodiment, the culture medium and the support member contain a plant pathogen chemoattractant for the same plant pathogen. Typically, the support member and the culture medium contain the same plant pathogen chemoattractant. Typically, the concentration of the plant pathogen chemoattractant in the culture medium is higher than the concentration of plant pathogen chemoattractant on the support member. This creates a concentration gradient. Due to the concentration gradient created by the higher level of chemoattractant in the culture medium compared to the lower level of chemoattractant on the support member, the spores specifically attracted to the chemoattractant will travel by chemotaxis, through the pores of the filter to reach the culture medium.

In one embodiment, the culture medium comprises antibiotics and/or nutrients. In one embodiment, the culture medium comprises antibiotics that prevent the growth of bacteria. In one embodiment, the culture medium comprises nutrients. In one embodiment, the culture medium comprises alcohols. In one embodiment, the culture medium comprises amino acids. In one embodiment the culture medium comprises pesticides or fungicides. The presence of antibiotics, pesticides and/or fungicides allows the growth of the plant pathogen of interest and prevents the growth of pathogens not of interest, for example other fungi and bacteria that have entered the device. In one embodiment the culture medium comprises nitrobenzenes or isoflavonoids. The culture medium can contain any combination of agar, nutrients, alcohols, amino acids, fungicides, pesticides, antibiotics, nitrobenzenes, plant extracts and/or isoflavonoids. In one embodiment, the culture medium comprises a buffer. The person skilled in the art will be able to select an appropriate buffer from commercially available buffers. In one embodiment, the buffer is optimal for the survival of *Phytophthora*.

In some embodiments, the device comprises a first culture medium (3) and a second culture medium (5). In one embodiment, the first and second culture media contain a plant pathogen chemoattractant for the same plant pathogen. Typically, the first and second culture media contain the same plant pathogen chemoattractant. In one embodiment, the concentration of the plant pathogen chemoattractant in the second culture medium is higher than the concentration of plant pathogen chemoattractant in the first culture medium. This creates a concentration gradient. Due to the concentration gradient created by the higher level of chemoattractant in the second culture medium compared to the lower level of chemoattractant in the first culture medium, the spores specifically attracted to the chemoattractant will travel by chemotaxis, through the pores of the first and second filter, to reach the second culture medium.

In some embodiments, the first and/or second culture medium can comprise additional plant pathogen chemoattractants, for example one, two, three, four, five, six, seven, eight, nine, ten, eleven, twelve, thirteen, fourteen, fifteen, sixteen, seventeen, eighteen, nineteen, twenty or twenty or more additional plant pathogen chemoattractants. In some embodiments the first and second culture medium comprise the same one, two, three, four, five, six, seven, eight, nine, ten, eleven, twelve, thirteen, fourteen, fifteen, sixteen, seventeen, eighteen, nineteen or twenty or more additional plant pathogen chemoattractants. In some embodiments the first and second culture mediums comprise different additional plant pathogen chemoattractants. In this embodiment, the first and second culture mediums comprise different combinations of plant pathogen chemoattractants.

The first and second culture medium can contain one or more additional plant pathogen chemoattractants wherein the concentration of the one or more additional plant pathogen chemoattractant in the second culture medium is higher than the concentration of the additional plant pathogen chemoattractant in the first culture medium. In another embodiment, the first and second culture medium can contain additional plant pathogen chemoattractants, wherein the one or more additional plant pathogen chemoattractants are not present in a concentration gradient. In this embodiment, the first and second culture mediums comprise the same concentration of each of the one or more additional plant pathogen chemoattractants.

One or more of the culture media aids growth of the plant pathogen spore and can have many different compositions, depending on the pathogen spore being detected, which will be well understood by the person skilled in the art. In one embodiment, one or more of the culture media is optimal for the survival of *Phytophthora*.

In one embodiment, one or more of the culture media comprises antibiotics and/or nutrients. In one embodiment, one or more of the culture media comprises antibiotics that prevent the growth of bacteria. In one embodiment, one or more of the culture media comprises nutrients. In one embodiment, one or more of the culture media comprises alcohols. In one embodiment, one or more of the culture media comprises amino acids. In one embodiment one or more of the culture media comprises pesticides or fungicides. The presence of antibiotics, pesticides and/or fungicides allows the growth of the plant pathogen of interest and prevents the growth of pathogens not of interest, for example other fungi and bacteria that have entered the device. In one embodiment one or more of the culture media comprises nitrobenzenes or isoflavonoids. One or more of the culture medium can contain any combination of agar, nutrients, alcohols, amino acids, fungicides, pesticides, antibiotics, nitrobenzenes, plant extracts and/or isoflavonoids.

In one embodiment, the first and/or second culture medium comprises a buffer. The buffer maintains the pH of the culture medium and aids the growth of the plant pathogen. In one embodiment, the first culture medium comprises a buffer and the second culture medium comprises a buffer in a lower concentration than the buffer of the first culture medium. The lower concentration of buffer in the second culture medium means that the pH level of the second culture medium can be altered. In one embodiment, the first culture medium comprises a buffer and the second culture medium does not comprise a buffer. The absence of buffer in the second culture medium means that the pH level of the second culture medium can be altered. These embodiments are particularly useful when the detection means is a pH indicator. The person skilled in the art will be able to select an appropriate buffer from commercially available buffers. In one embodiment, the buffer is optimal for the survival of *Phytophthora*.

In one embodiment, the first culture medium has the same composition as the second culture medium. In another embodiment, the first culture medium has a different composition to the second culture medium.

The person skilled in the art will be able to select an appropriate culture medium from commercially available culture media. Further, the person skilled in the art will be able to synthesize an appropriate culture medium from standard literature protocols.

In one embodiment, the first and/or second culture medium is an agar culture medium and is therefore semi-solid or in gel form. In this embodiment, each respective filter is placed on its respective culture medium when the culture medium solidifies during the preparation of the device. In another embodiment, the first and/or second culture medium is a liquid culture medium.

The device of the invention can contain other culture media in addition to the first and optionally second culture media. Accordingly, in one embodiment, there can be two, three, four, five, six, seven, eight, nine or ten culture media present in the device for detecting a plant pathogen. The device comprises alternating layers of filter and culture medium. In some embodiments, the device comprises two or more, three or more, four or more, five or more, six or more, seven or more, eight or more, nine or more, ten or more alternating layers of filters and culture medium.

The support member (1) is adjacent to the first filter (2). The first filter (2) is adjacent to the first culture medium (3). In some embodiments, the first culture medium (3) is adjacent to a second filter (4). in some embodiments, the second filter (4) is adjacent to a second culture medium (5). The support member (1) can be connected to the first filter (2) by any suitable means. The first filter (2) can be connected to the first culture medium (3) by any suitable means. The first culture medium (3) can be connected to a second filter (4) by any suitable means. The second filter (4) can be connected to a second culture medium (5) by any suitable means. In one embodiment, the means for connecting each filter to a support member and/or culture medium may be physical means or support. The physical means or support can be of any suitable size, shape or material that allows the support member, first filter and first culture medium to remain connected. In some embodiments, the physical means or support can be of any suitable size, shape or material that allows the support member, first filter, first culture medium, second filter and second culture medium to remain connected.

In some embodiments, the device further comprises a container wherein the container holds the filter and culture medium. The container can be of any suitable shape, size or material that allows it to hold the filter and culture medium, and typically allows the device to be placed as a whole in soil. In some embodiments, the container holds the filter and culture medium, wherein the pores of the filter are not covered by the container. In this embodiment, the pores of the filter are exposed to soil when the device is in use. Alternatively, for example, when culture media is in a gel form, a container is not present. In some embodiments, the container is plastic.

In some embodiments, the device further comprises a container wherein the container holds the first filter, first culture medium, second filter and second culture medium. The container can be of any suitable shape, size or material that allows it to hold the first filter, first culture medium, second filter and second culture medium and typically allows the device to be placed as a whole in soil. In some embodiments, the container holds the first filter, first culture medium, second filter and second culture medium wherein the pores of the first filter are not covered by the container. In this embodiment, the pores of the first filter are exposed to soil when the device is in use. Alternatively, the pores of the first filter and/or second filter are not exposed directly to the soil and the support member is in direct contact with the soil. Alternatively, for example, when the first and second culture media are in a gel form, a container is not present. In some embodiments, the container is plastic.

The device of the invention also comprises a detection means. The detection means is suitable to detect the plant pathogen of interest and enables the user of the device to determine whether the plant pathogen of interest is present in the area being tested.

In one embodiment, the detection means comprises a pH indicator. The pH indicator is typically present in the culture medium and provides the pH of the culture medium. Plant pathogen spores present in the culture medium acidify the culture medium and induce a change of pH in the culture medium. A plant pathogen spore can release metabolites to induce a change in pH. Different plant pathogen spores induce different pH levels and the level of pH can therefore be used to indicate the presence or absence of a plant pathogen spore in the culture medium. In some embodiments, the pH indicator will detect a pH range specific to the plant pathogen spore to be detected. In some embodiments, the pH of the culture medium is about 1 pH unit lower in the presence of a plant pathogen spore than the pH value of the culture medium in the absence of the plant pathogen spore. In some embodiments, the pH of the culture medium is more than 1 pH unit lower in the presence of a plant pathogen spore than the pH value of the culture medium in the absence of the plant pathogen spore. In some embodiments, the pH indicator changes colour in the presence of a plant pathogen spore. In some embodiments, the pH indicator will change colour in the presence of *Phytophthora*. A person skilled in the art will be able to select an appropriate pH indicator that detects the presence of the plant pathogen spore of interest from commercially available indicators. In some embodiments, the pH indicator is adapted to indicate to the user that the presence of plant pathogen spore at the pH indicator has been detected. In some embodiments, the pH indicator can be connected to a visual display unit or a computer. In one embodiment the pH indicator is connected to a digital indicator of pH. In other embodiments, the presence of a plant pathogen spore at the pH indicator triggers a further event or series of events, optionally utilising a computer or visual output, to indicate the presence of a plant pathogen spore.

When a pH indicator is used as a detection means, the first culture medium or second culture medium (if present) typically contains a low concentration of buffer or no buffer at all, to ensure that the pH changes as the plant pathogen spores arrive in the culture medium and can be detected by means of a pH change.

In another embodiment, the detection means is an electrochemical detection method. In an alternative embodiment, the detection means is biochemical reaction, such as enzymatic activity or protein interactions. This also detects a change in pH and therefore conductivity of the culture medium/media. In other embodiments, the detection means comprises an immunoassay or lateral flow detection. The lateral flow or immunoassay, electrochemical detection or biochemical method can detect the presence of a plant pathogen spore in the first culture medium or second culture medium (if present).

In one embodiment, the detection means is coupled to a computer. The detection means can be coupled to the computer by a wireless chip, via Bluetooth or infrared.

In one embodiment, there is provided a device for detecting a plant pathogen spore in soil or water comprising: a support member (1) containing a at least one plant pathogen chemoattractant, a first filter (2) having a plurality of pores, a first culture medium (3) containing a at least one plant pathogen chemoattractant, a second filter (4) having a plurality of pores, wherein the size of the pores in the second filter is smaller than the size of the pores in the first filter, a second culture medium (5) containing a at least one plant pathogen chemoattractant, wherein the concentration of at least one plant pathogen chemoattractant in the second culture medium is higher than the concentration of at least one plant pathogen chemoattractant in the first culture medium, and a detection means, wherein the support member (1) is adjacent to the first filter (2), the first filter (2) is adjacent to the first culture medium (3), the first culture medium (3) is adjacent to the second filter (4) and the second filter (4) is adjacent to the second culture medium.

In a second aspect, the present invention provides a method of detecting a plant pathogen comprising: (a) placing the detection device of the invention in soil or water, and (b) using the detection means to determine the presence or absence of pathogen.

In a third aspect, the present invention provides the use of the detection device for detecting a plant pathogen spore.

Preferred features for the second and subsequent aspects of the invention are as for the first aspect of the invention mutatis mutandis. Further, features described in relation to one aspect or embodiment of the invention can be included in another aspect or embodiment of the invention, or excluded where not essential.

The person skilled in the art will realise that the embodiments described herein are not limited and that support members, filters or culture media could be produced using other materials and compositions to produce the same effect.

Example 1. Detection of *Phytophthora*

60 g of rye grain was soaked for 24 hours in distilled water, after which, the supernatant was poured off and stored for later use. The rye grain was blenderised, and then heated at 68° C. for 1 hour. The rye solution was combined with the supernatant, and filtered through 2 layers of cheesecloth. 20 g of sucrose, 15 g of agar, and 0.04 g of bromocresol purple were added to the rye solution, and the media was made to 1 L with distilled water. The media was autoclaved at 15 psi for 20 minutes, and once cooled to −40° C., antibiotics were added (0.02 g/L of rifampicin, 0.05 g/L of polymixin B, 0.10 g/L of ampicillin, and 0.05 g/L of vancomycin). The media was poured into 100×15 mm petri plates, and once cooled, were stored in the dark at 4° C.

Inoculation with *Phytophthora infestans*

Growth media plates were inoculated with *Phytophthora infestans* by placing two 0.5×1 cm squares from an actively growing culture in the centre of each plate. The plates were grown at 22° C. 12 plates were inoculated, and each day for 4 days, the pH of 3 plates were measured. As a control, growth media plates which were not inoculated with *Phytophthora infestans* were also monitored, and the pH measured.

Results

As shown in FIG. 5A, a colour change was observed in the device after the addition of *Phytophthora*. FIG. 5Ai shows the device without inoculation with *Phytophthora infestans* and FIG. 5Aii shows the colour change in the device 96 hours after inoculation with *Phytophthora* (Day 4). FIG. 5B is a graph depicting the pH change over 4 days after the inoculation of the media growth plates with *Phytophthora infestans* (Day 0: pH 6.20±0.02; Day 1: pH 6.14±0.02; Day 2: pH 6.07±0.01; Day 3: pH 6.04±0.01; Day 4: pH 5.90±0.02). Values are averages of 3 repeats, and error bars are standard deviation. The pH change was significantly different to Day 0 on all days measured (Day 1 to 4), with unpaired t-tests giving p-values <0.05 on Day 1, and <0.001 on Day 2-4.

The invention claimed is:

1. A method for in-situ detection of microorganisms or plant pathogens directly at a site of soil or water employing a detection device comprising:

placing a support member of the detection device in contact with the soil or water, wherein the support member contains a plant pathogen chemoattractant absorbed by the support member to attract the microorganisms or the plant pathogens in the soil or water into the detection device, wherein the support member is the only part of the device inserted into the soil or water and insertion is located in the soil or water at a location of plant growth or a location being considered for plant growth; and detecting the microorganisms or the plant pathogens directly at the site of the soil or water after placing the support member of the detection device in contact with the soil or water;

wherein the support member comprises material that allows the microorganisms or the plant pathogens to flow within the detection device from one end of the support member to another end of the support device via a filter positioned within the detection device that selectively allows only the microorganisms or the plant pathogens to be detected to reach a culture medium also within a container and connected to the filter; and wherein the culture medium contains a plant pathogen chemoattractant which attracts the microorganisms or the plant pathogens, and the culture medium further contains a detection means capable of detecting the microorganisms or the plant pathogens.

2. The method according to claim 1, wherein the culture medium aids growth of the plant pathogen to be detected.

3. The method according to claim 1, wherein the detection means is a pH indicator.

4. The method according to claim 3, wherein the chemoattractant is present at a higher concentration at the end of the support member adjacent to the culture medium than at the end of the support member that is placed in contact with the soil or water.

5. The method according to claim 1, wherein the support member includes a concentration gradient of chemoattractant.

6. The method according to claim 1, wherein the culture medium comprises a liquid culture medium.

7. The method according to claim 1, wherein the culture medium comprises an agar culture medium.

8. The method according to claim 1, wherein the culture medium comprises an antibiotic.

9. The method according to claim 1, wherein the culture medium comprises a fungicide.

10. The method according to claim 1, wherein the culture medium comprises a nutrient for the pathogen to be detected.

11. The method according to claim 1, wherein the method is free of manual preparation of a sample obtained from the soil or water and is free of external laboratory analysis so that a user determines whether the microorganisms or plant pathogens are present while at the site of the soil or water.

12. The method according to claim 1, wherein the support member comprises a plastic dipstick and a membrane of nitrocellulose or nylon is coated on the dipstick.

13. The method according to claim 1, wherein pores of the filter are not covered by the container and are exposed to the soil or the water when the detecting device is in use.

14. The method according to claim 1, wherein a concentration of the chemoattractant in the culture medium is higher than a concentration of the chemoattractant in the support member.

15. The method according to claim 1, wherein the support member is tapered.

* * * * *